US008432542B2

(12) United States Patent
Marple et al.

(10) Patent No.: US 8,432,542 B2
(45) Date of Patent: Apr. 30, 2013

(54) FIBER OPTIC PROBES UTILIZING GRIN LENSES FOR SPATIALLY PRECISE OPTICAL SPECTROSCOPY

(76) Inventors: Eric T. Marple, Loxahatchee, FL (US); Kirk D. Urmey, West Milton, OH (US)

( * ) Notice: Subject to any disclaimer, the term of this patent is extended or adjusted under 35 U.S.C. 154(b) by 157 days.

(21) Appl. No.: 13/206,264

(22) Filed: Aug. 9, 2011

(65) Prior Publication Data

US 2012/0176613 A1    Jul. 12, 2012

Related U.S. Application Data

(60) Provisional application No. 61/431,321, filed on Jan. 10, 2011.

(51) Int. Cl.
*G01N 21/64* (2006.01)
*G01N 21/65* (2006.01)

(52) U.S. Cl.
USPC ........... 356/301; 356/318; 356/417; 359/629; 359/351

(58) Field of Classification Search .................. 356/301, 356/318, 417; 359/629, 634; 385/12, 147
See application file for complete search history.

(56) References Cited

U.S. PATENT DOCUMENTS

| 4,573,761 | A |   | 3/1986  | McLachlan et al. |
|-----------|---|---|---------|------------------|
| 5,112,127 | A |   | 5/1992  | Carrabba et al.  |
| 5,293,872 | A |   | 3/1994  | Alfano et al.    |
| 5,402,508 | A |   | 3/1995  | O'Rourke et al.  |
| 5,410,413 | A | * | 4/1995  | Sela ............................... 356/446 |
| 5,751,416 | A |   | 5/1998  | Singh et al.     |
| 5,774,610 | A |   | 6/1998  | O'Rourke et al.  |
| 5,911,017 | A |   | 6/1999  | Wach et al.      |
| 6,028,666 | A |   | 2/2000  | Boss et al.      |
| 6,088,166 | A |   | 7/2000  | Lee              |
| 6,172,817 | B1|   | 1/2001  | Senapati et al.  |
| 6,208,783 | B1|   | 3/2001  | Wach             |
| 6,208,887 | B1|   | 3/2001  | Clarke           |
| 6,222,970 | B1|   | 4/2001  | Wach et al.      |
| H2002     | H |   | 11/2001 | McLachlan        |
| 6,690,966 | B1|   | 2/2004  | Rava et al.      |
| 6,737,649 | B2|   | 5/2004  | Webster          |
| 6,762,835 | B2|   | 7/2004  | Zhang et al.     |
| 6,809,813 | B2| * | 10/2004 | Bennett et al. ................. 356/301 |
| 7,148,963 | B2| * | 12/2006 | Owen et al. .................... 356/301 |
| 7,394,537 | B1|   | 7/2008  | Lindfors et al.  |
| 7,482,296 | B2|   | 1/2009  | Messerschmidt et al. |
| 7,499,153 | B2|   | 3/2009  | Puppels et al.   |
| 7,647,092 | B2|   | 1/2010  | Motz et al.      |
| 7,714,998 | B2|   | 5/2010  | Furman et al.    |
| 8,175,423 | B2|   | 5/2012  | Marple et al.    |

(Continued)

OTHER PUBLICATIONS

PCT/US2011/047122, International Search Report and Written Opinion of the International Searching Authority, Dec. 12, 2011.
Santos et al., *Fiber-Optic Probes for In Vivo Raman Spectroscopy in the High-Wavenumber Region*, Anal. Chem. 2005, 77, 6747-6752.
Utzinger et al., *Fiber optic probes for biomedical optical spectroscopy*, Journal of Biomedical Optics 8(1), 121-147, Jan. 2003.

(Continued)

*Primary Examiner* — Layla Lauchman
(74) *Attorney, Agent, or Firm* — Paul Diamond, Esq.; Diamond Law Office, LLC

(57) ABSTRACT

The invention provides improved fiber optic probe assemblies which utilize a configuration of gradient index (GRIN) lenses to deliver light to a focal point and collect light for analysis from the same focal point. Also provided are methods for manufacturing the probe assemblies and related methods of spatially precise spectroscopy using the probe assemblies.

30 Claims, 14 Drawing Sheets

U.S. PATENT DOCUMENTS

| | | |
|---|---|---|
| 2003/0191398 A1 | 10/2003 | Motz et al. |
| 2004/0073120 A1 | 4/2004 | Motz et al. |
| 2004/0081397 A1 | 4/2004 | Liu et al. |
| 2004/0267110 A1 | 12/2004 | Tremble |
| 2006/0139633 A1 | 6/2006 | Puppels et al. |
| 2009/0231578 A1 | 9/2009 | Ling et al. |
| 2009/0302205 A9 | 12/2009 | Olsen et al. |
| 2009/0323076 A1 | 12/2009 | Li et al. |
| 2011/0135244 A1 | 6/2011 | Marple |

OTHER PUBLICATIONS

Reed et al., *Gradient-index fiber-optic microprobes for minimally invasive in vivo low-coherence interferometry*, Optics Letters vol. 27, No. 20, 1794-1796, Oct. 15, 2002.

Ansari et al., *Compact, Non-Contact Fiber-Optic Probe for Diagnosis of Eye Diseases*, NASA Tech Briefs, Feb. 1998, vol. 22, No. 2, p. 82.

\* cited by examiner

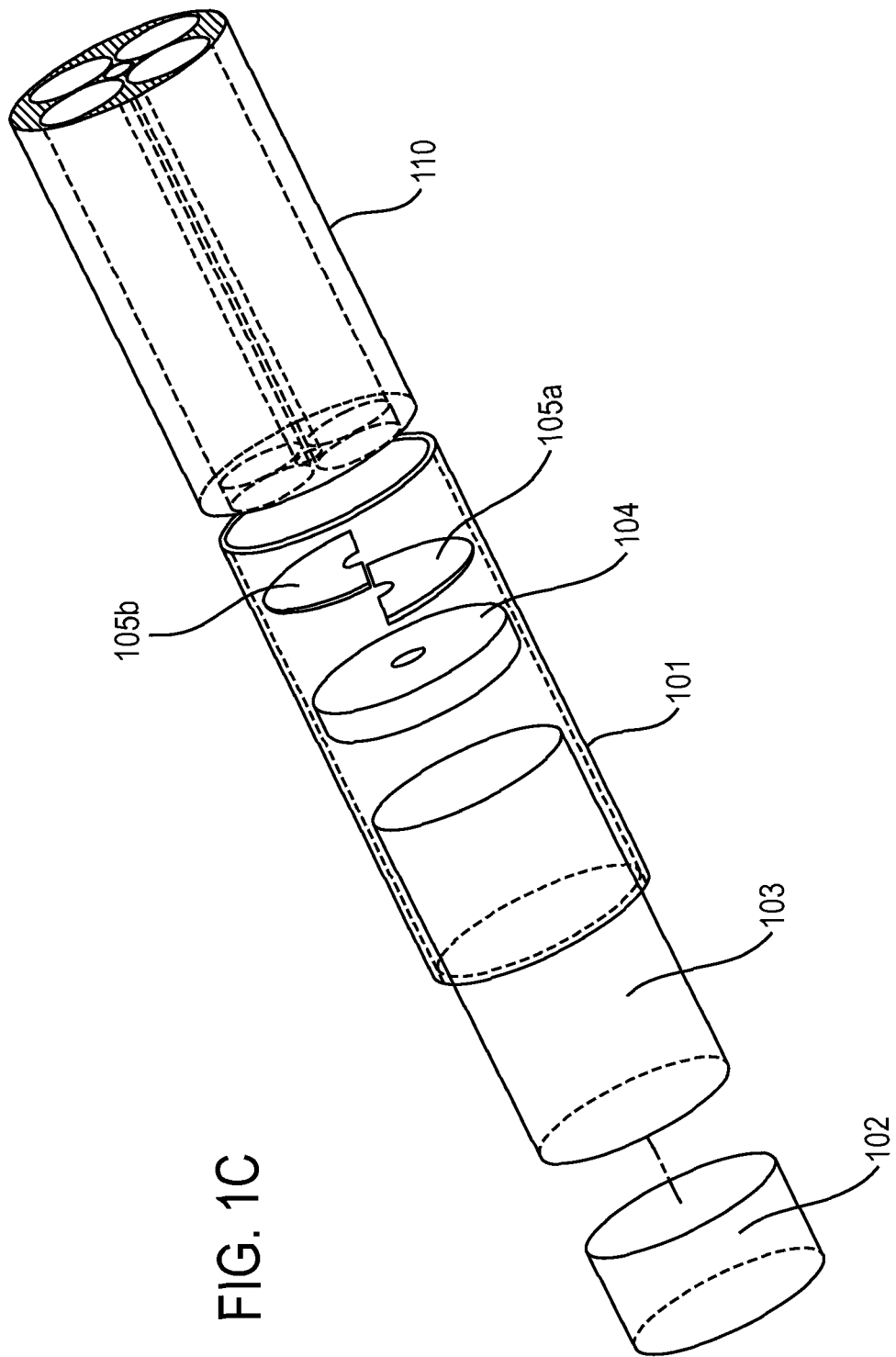

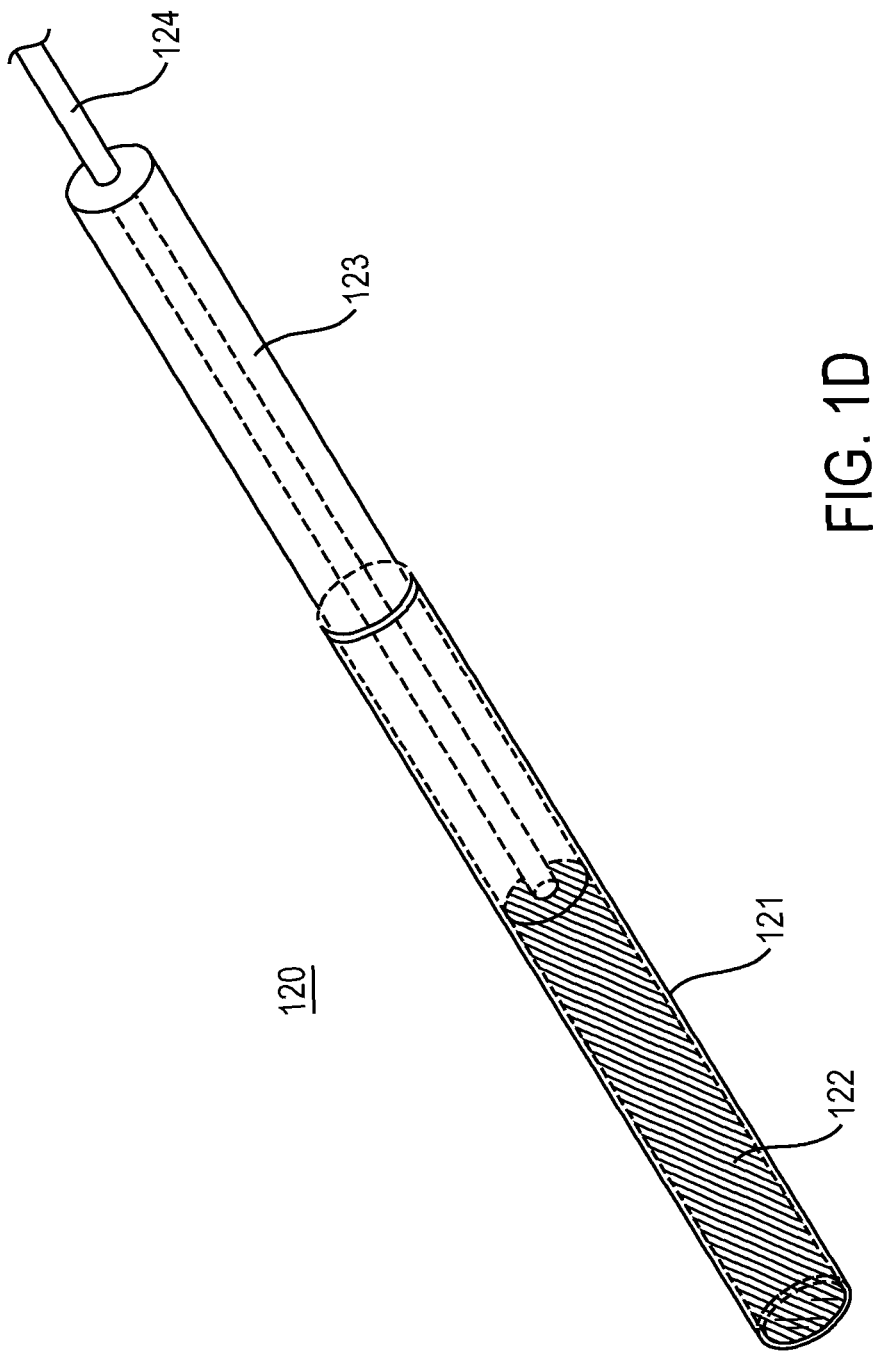

FIBER OPTIC PROBES UTILIZING GRIN LENSES FOR SPATIALLY PRECISE OPTICAL SPECTROSCOPY

CROSS-REFERENCE TO RELATED APPLICATIONS

This application claims the benefit of U.S. provisional patent application Ser. No. 61/431,321 filed Jan. 10, 2011, which is hereby incorporated by referenced in its entirety.

FIELD OF THE INVENTION

The invention relates to the field of fiber optic spectroscopy probes.

BACKGROUND OF THE INVENTION

Light-scattering spectroscopy entails illumination of a substance and analyzing light that is scattered at angles relative to the incident source. The photon-matter interactions of the scattering events may be either elastic or inelastic. In an inelastic event, a photon's energy (wavelength) changes as a result of the light-matter interaction. In an elastic event, a photon's energy (wavelength) does not change. Absorption, the phenomena in which a fraction of photons are entirely absorbed, also plays a role in light-scattering spectroscopies.

Raman, diffuse reflectance, and fluorescence spectroscopies are of particular interest as they relate to vibrational and nonvibrational photonic responses of a material. The Raman effect describes a subtle light-matter interaction. Minute fractions of light illuminating a substance are Raman-scattered in random directions. Raman-scattered light is color shifted from the incident beam (usually a laser). The color frequency shifts are highly specific as they relate to molecular bond vibrations inducing molecular polarizability changes. Raman spectroscopy is a powerful technique for chemical analysis and monitoring. Analysis of the resulting low light levels requires sophisticated, expensive instrumentation and technical complexity. The collection of Raman spectra in the fingerprint (FP) region, i.e., approximately 200 to 2,000 $cm^{-1}$, through optical fibers is complicated by Raman signal from the fibers themselves. A band-pass (laser line) filter may be used at the delivery end of a delivery fiber to remove the silica Raman bands arising from the fiber itself before illuminating a sample. A long-pass filter may be disposed before a collection fiber so that only the Stokes scattered light enters the fiber. Filtering for optical fiber-based Raman spectroscopy is described, for example in U.S. Statutory Invention Registration No. H002002.

Specular reflectance relates to a surface's mirror-like aspects. Diffuse reflectance relates to light that is elastically scattered from the surface of a material at diffuse angles relative to the incident beam. For example, a projector screen diffusely reflects light while a glossy, newly waxed car has a high specular component. Diffuse reflectance spectroscopy is important for chemical analysis as well as measuring visual perception.

Fluorescence relates to substances which absorb light at one wavelength then re-emit it at a longer wavelength as a result of electronic transitions. As an example, a "highlighter" felt-tip marker appears to "glow" green as it absorbs blue and ultraviolet light then emits it as green. Fluorescence provides a powerful technique for chemical monitoring.

Raman spectroscopy involves energizing a sample with a high-power, narrow-wavelength energy source, such as a laser. The laser photons induce low intensity light emissions as wavelengths shift. The Raman effect is an inelastic scattering of photons. The emitted Raman light is collected and analyzed using a spectrometer or light detector. The spectral positions (colors) of the shifts provide fingerprints of the chemicals in the sample. Thus, Raman spectroscopy provides a means for chemical identification. The intensity of the shift (the spectral peak height) correlates to chemical concentration. Thus, a properly calibrated instrument provides chemical content and concentration. In practicality, Raman spectroscopy is technically complex and requires sophisticated, expensive instrumentation. Raman spectroscopy-based methods and apparatuses are disclosed, for example, in U.S. Pat. Nos. 5,293,872; 6,208,887 and 6,690,966, and in U.S. Publication No. 2004/0073120.

Laser-induced breakdown spectroscopy (LIBS) is another optical analytical method that may be employed using fiber optics. LIBS is disclosed in U.S. Pat. Nos. 5,751,416; 6,762,835; and 7,394,537.

Optical coherence tomography (OCT) is an optical signal acquisition and processing method. It captures micrometer-resolution, three-dimensional images from within optical scattering media (e.g., biological tissue). Optical coherence tomography is an interferometric technique, typically employing near-infrared light. The use of relatively long wavelength light allows it to penetrate into the scattering medium. Confocal microscopy, another similar technique, typically penetrates less deeply into the sample. U.S. Publication No. 2004/0267110 discloses an OCT system and its use.

Dispersive spectroscopic techniques typically utilize a slit at the entrance of the spectrometer to control the input of light which affects the resolution of the spectra. Wider slits result in a lower resolution of the spectra. The larger angle of input light (higher NA) the lower the resolution of the spectra. The lower the resolution of the spectra results in more difficulty in resolving individual peaks. The narrower the slit is, the higher resolution obtained, but at the detriment of total light input to the spectrometer. This will result in longer acquisition times unless the input (fiber diameter) is the same as the slit width.

Since fingerprint region Raman fiber optic probes with high spatial resolution or controllable spatial resolution has historically been difficult to manufacture, this has been an area of concentration for the design of the present invention. Many other spectroscopic techniques including high wavenumber Raman will also work with the probe design of the present invention. U.S. Publication No. 2006/0139633 discloses the use of high wavenumber Raman spectroscopy for the characterization of tissue. Santos et al., *Fiber-Optic Probes for In Vivo Raman Spectroscopy in the High-Wavenumber Region*, Anal. Chem. 2005, 77, 6747-6752 discloses known probe designs for high wavenumber Raman spectroscopy.

To the inventors' knowledge, to this point no optical fiber probe has achieved the combination of very small size, robustness, ease of construction, high spatial resolution, and high collection efficiency. In addition, the ability to collect both polarization states, fluorescence, diffuse reflectance and OCT all from the same probe looking at the same spot to collect the spectra has not before been realized. The probes of the present invention meet the above criteria utilizing GRIN lenses and other optical elements and fiber optics, making them well adapted for industrial, scientific and medical applications.

SUMMARY OF THE INVENTION

The probe design of the present invention utilizes gradient index (GRIN) lenses to focus the laser delivery spot and cause the collection spot to be at the same or approximately the same focal point, or at any desired focal point for each.

Without limitation, the invention provides the following embodiments:

One embodiment of the invention provides a fiber optic probe assembly having a distal sampling end and a proximal end, said probe including:

(a) a front (distal) GRIN lens having a distal end, a proximal end, a central (longitudinal) axis, a length and a transverse dimension (outer diameter);

(b) at least one collection GRIN lens having a distal end, a proximal end, a central axis, a length and a transverse dimension (outer diameter), the distal end of the at least one collection GRIN lens in optical communication with the proximal end of the front GRIN lens, (c) a collection optical fiber having a distal end, a proximal end and a central axis, the proximal end of at least one of the collection GRIN lenses being in optical communication with the collection optical fiber the central axis of the collection optical fiber at its distal end being parallel to the central axis of the front GRIN lens, and the transverse dimension (outer diameter) of the distal end of the collection optical fiber being within the footprint (outer diameter; transverse dimension) of the front GRIN lens; and (d) a light delivery optical fiber having a distal end, a proximal end and a central axis, its central axis at its distal end being parallel to the central axis of the front GRIN lens and its transverse dimension (diameter) at its distal end being within the footprint (outer diameter) of the front GRIN lens. In one variation, the distal end of the light delivery optical fiber is in optical communication with the proximal end of the front GRIN lens, one or more filters, lenses or polarizers optionally disposed provided there between. The length of the front GRIN lens may be selected to reduce or eliminate the overlap of light collection and light delivery pathways within the front GRIN lens for a preselected illumination wavelength of light. The front lens may be shortened to less than 0.25 pitch (from 0.25 pitch or greater than 0.25 pitch), based on the preselected illumination wavelength of light such as may be selected to perform a particular type of spectroscopy. The shortening of length may, for example, be a reduction of 5%, or at least 5%, in length from 0.25 pitch. If GRIN lenses of suitable length are available, they may be selected for use, rather than shortened to length. In one variation, the distal end of the light delivery optical fiber is in optical communication with the proximal end of the front GRIN lens, one or more filters, lenses or polarizers optionally disposed provided there between. The length of the front GRIN lens may be selected to reduce or eliminate the overlap of light collection and light delivery pathways within the front GRIN lens for a preselected illumination wavelength of light. The front lens may be shortened to less than 0.25 pitch (from 0.25 pitch or greater than 0.25 pitch), based on the preselected illumination wavelength of light such as may be selected to perform a particular type of spectroscopy.

In one version of the embodiment, a longitudinal hole is disposed in and passes through the center of the front GRIN lens, and the probe further includes:

a front laser delivery GRIN lens having a distal end and a proximal end surrounded by an optically opaque encasement inserted into said hole;

a back laser delivery GRIN lens having a distal end and a proximal end, the distal end thereof in optical communication with the proximal end of the front laser delivery GRIN lens and the proximal end thereof in optical communication with the distal end of the light delivery optical fiber; and optionally, one or more filters disposed between the front and back laser delivery GRIN lenses. The front laser delivery GRIN lens has at least substantially the same refractive index gradient profile as the portion of the front GRIN lens that existed in the space occupied by the hole before the hole was formed. The encasement may, for example, be a metal tube.

In a different version of the embodiment, a longitudinal hole is disposed in and passes through the front GRIN lens, for example, through the center, and the light delivery fiber is inserted into said hole such that the distal end of the light delivery fiber is disposed at or near the distal end of the front GRIN lens, the distal-proximal orientation of each of said components being codirectional, i.e., the proximal end of each component disposed in a common direction and the distal end of each component disposed toward a common opposite direction. There may be no GRIN lens at all at the distal end of the light delivery fiber or at any point in the light delivery pathway. This version of the embodiment is particularly useful for a spectroscopy where the excitation wavelength may be absorbed by the front lens, such as UV fluorescence spectroscopy. In a variation, at least the part of the light delivery fiber inserted in the hold in the front GRIN lens is surrounded by an optically opaque tube, such as a metal tube. Optionally, the tube may extend further proximally.

In still another version of the embodiment, the probe further includes a light delivery GRIN lens having a distal end, a proximal end, a central axis, a length and an outer diameter, the proximal end of the light delivery GRIN lens in optical communication with the distal end of the light delivery optical fiber, wherein a longitudinal hole is disposed in and passes through a collection GRIN lens and the distal end of the laser delivery GRIN lens is inserted into said hole. In one variation of this version of the embodiment, there is a single collection GRIN lens selected to provide to the collection optical fiber/fiber bundle with which it optically communicates collected light at the proximal end of the collection GRIN with a numerical aperture/diameter the same as or near the numerical aperture of said collection optical fiber.

The invention also provides spectroscopic apparatuses including the probe assemblies and methods for manufacturing the probe assemblies.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

DETAILED DESCRIPTION OF THE INVENTION

Figure 1A:
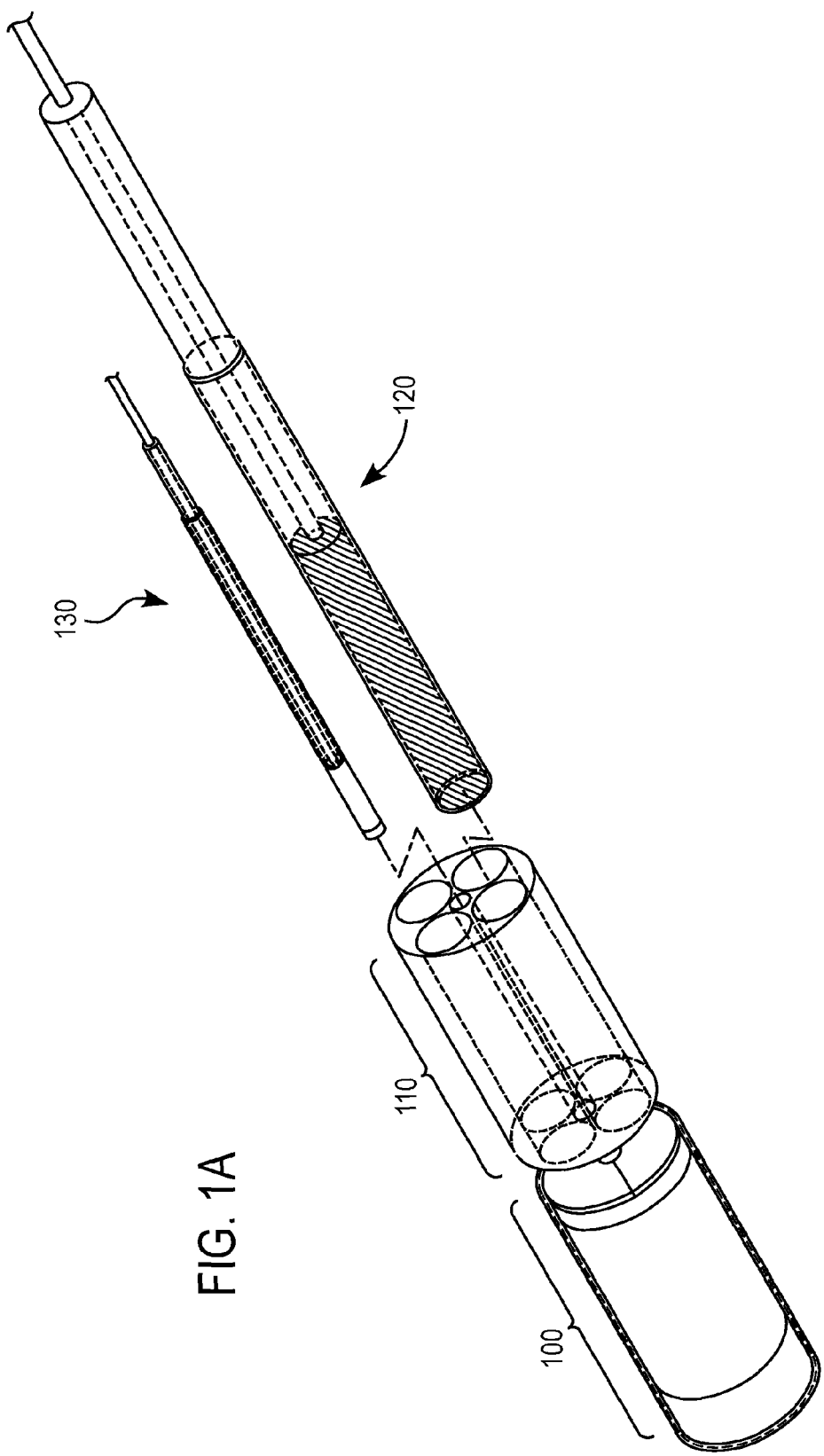
FIG. 1A: Assembly of preferred embodiment only one collection sub-assembly of 4 possible is shown.

The present invention provides miniature fiber optic probes that utilize gradient index (GRIN) lenses to focus the light delivery spot to a focal volume or point and cause collection of light to be obtained from the same or approximately the same focal volume point, whilst maximizing the amount of light collected from the sample. More generally, any desired focal point/volume can be selected for each of the light delivery and light collection paths.

To manipulate the spot size(s) of the light delivery and the collection, an understanding of the GRIN lens performance is required. There are two important aspects of GRIN lenses that must be understood to understand this invention's design. The first aspect is the effective useful diameter of the GRIN lens when coupled to a 0.22 NA fiber. A 1.8 mm diameter GRIN lens (GoFoton, Japan, previously Nippon Sheet glass (NSG), SELFOC micro lens™) which is 0.46 NA and 0.25 pitch when you put a 0.22 NA 100 micron core fiber to this lens the collimated beam is approximately 0.84 mm in diameter which means that the lens could be 0.84 mm in diameter and perform as well as the 1.8 mm GRIN lens that it started out as. The present invention provides, among other things, for grinding GRIN lenses down to diameters closer to that which is effectively useful in the fiber optic probes. The second aspect is related to the image size for a particular lens combination. For example, if a 1.8 mm diameter, 0.25 pitch, 0.46 NA GRIN lens is butted to a like 1.8 mm diameter lens, the image of a fiber as viewed through this lens pair is practically the same diameter as the input fiber diameter. Additionally, if a 1 mm diameter, 0.25 pitch, 0.46 NA GRIN lens is abutted to a 1.8 mm diameter, 0.25 pitch, 0.46 NA GRIN lens, the image of a fiber which is butted to the 1 mm GRIN lens and viewed looking at the exit surface of the 1.8 mm diameter GRIN lens is increased by the ratio of the original diameters of the lenses. For example a 100 micron input fibers diameter is imaged as approximately 180 microns. Particular desired image/spot size(s) and spatial resolution(s) can be readily obtained by selecting the appropriate combination of GRIN lenses.

One embodiment of the invention provides a fiber optic probe assembly having a distal sampling end and a proximal end, said probe including:
(a) a front (distal) GRIN lens having a distal end, a proximal end, a central (longitudinal) axis, a length and an outer diameter;
(b) at least one collection GRIN lens having a distal end, a proximal end, a central axis, a length and a outer diameter, the distal end of the at least one collection GRIN lens in optical communication with the proximal end of the front GRIN lens,
(c) a collection optical fiber or optical fiber bundle having a distal end, a proximal end and a central axis,
the proximal end of at least one of the collection GRIN lenses being in optical communication with the collection optical fiber or optical fiber bundle,
the central axis of the collection optical fiber at its distal end being parallel to the central axis of the front GRIN lens, and
the transverse dimension (outer diameter) of the distal end of the collection optical fiber or collection optical fiber bundle being within the footprint (outer diameter) of the front GRIN lens. The at least one collection GRIN lens is at least partially within the footprint of the front GRIN lens. A high numerical aperture NA front GRIN lens, while the collection GRIN lens has a lower NA which is at least substantially the same as the collection optical fiber or optical fiber bundle to which it is coupled. This allows a large amount of light to be collected at the distal sampling end of the probe, yet efficiently transmitted into the collection optical fiber or optical fiber bundle.

The probe assembly of the embodiment may further provide for light delivery and include a light delivery optical fiber having a distal end, a proximal end and a central axis, its central axis at its distal end being parallel to the central axis of the front GRIN lens and its transverse dimension (outer diameter) at its distal end being within the footprint (outer diameter) of the front GRIN lens. In one variation, the distal end of the light delivery fiber is disposed proximally to the proximal end of the front GRIN lens and optically communicates therewith so that both the illumination and collection light paths each pass through the front GRIN lens. This permits the light delivery path and light collection to have the same or approximately the same focal points or volumes. Still other variations are also provided by the invention. In operation, the laser delivery optical fiber is connected at its proximal end to a laser or other light source and the at least one collection optical fiber is connected at its proximal end to a light analyzer such as a spectrometer, interferometer or light detector.

As further described herein, probes according to the invention may be constructed from subassemblies, which together form the probe assemblies of the invention. Various filters, windows and/or polarizers may be provided between optically communicating components of the probe. The probe may optionally further include one or more optional lenses distal to the distal end of the front GRIN lens, such as focusing lenses used to adjust desired depth of sampling and/or optical assemblies such as side viewing assemblies including prisms, mirrors or the like, one or more windows, and/or filters.

The length of the front GRIN lens is preferably selected so that the laser delivery light path(s) and the collection light path(s) do not intersect at a focal point within the front GRIN lens itself, but instead intersect at a focal point distal to the distal end of the front GRIN lens. In general, the length of the front GRIN lens may be selected so that for a particular wavelength of light the collection and illumination light paths in the front GRIN lens do not overlap at all, or for example, at least 98% do not overlap (no more than 2% overlap). In this manner, signal noise from excitation of the front GRIN lens itself is minimized and virtually eliminated from the collection light. The lengths of commercially available GRIN lenses are reduced, if necessary, to the lengths needed, for example by grinding or polishing, before assembly of the probe.

In practice, the components of the probe that are in optical communication are butted up against one another, directly or indirectly if intervening components such as filters or polarizers are present, and may or may not be joined using optically transparent epoxy, as known in the art. Optical coupling of components means bringing them into the necessary proximity and position, including alignment, for their operation according to the invention, via optical communication with one another. Optical coupling may, but need not necessarily include physically joining some or all of the components with an optical adhesive such as an optical epoxy. Optical coupling may but need not necessarily include using structures such as tubes or other structures to confine, position and align various components with respect to one another.

Conventional fiber bundle probes not utilizing GRIN lenses suffer from several problems that make them difficult to gather high quality spectra from the actual area of interest. The subject design of the present invention allows for a great deal of flexibility by easily being able to change many aspects of the design. Design criteria that are readily implementable with the probes of the invention include, for example, the laser spot size, collection spot size and angle of collection. This design allows multiple spectroscopic techniques to be housed in the same probe, all sampling from the same spot. In addition, the collection GRIN lens(es) can be made to function as a filter, like a pin hole or spatial filter, by selecting/adjusting its diameter and radial position behind the front GRIN lens to only accept light from the angles desired. This permits information from a only specific chosen volume to be collected. A particular collection GRINs lens numerical aperture (NA) for use in the probe can be obtained by reducing the NA of a starting (precursor) GRIN lens to a final desired NA for the collection GRIN lens, for example, by centerless grinding, or more generally by selection of a collection GRIN lens with an appropriate NA for use as the collection GRIN lens. Favorably, the probe design of the invention provides, among other embodiments, a high collection efficiency contact optical probe that can sample from precise depths of medical interest, such as within 200 microns of the probe tip.

A related embodiment of the invention provides a fiber optic probe assembly useful in spectroscopy that includes at least one light delivery GRIN lens having a proximal end, a distal end and an outer diameter that is optically coupled to the distal end of the light delivery optical fiber. The light delivery GRIN lens is a lens which is a small diameter and the NA of the lens closely matches the NA of the light delivery optical fiber butted to it. At a front GRIN lens length of 0.25 pitch, the focal point of the light delivery path is at the front (distal) surface of the front GRIN lens and in typical embodiments the collection light focal point would be the same. This causes undesirably background signal, such as Raman signal for Raman spectroscopy embodiments, to be generated from the front GRIN lens itself which interferes with light collected from a target sample. Therefore, in at least the embodiments of the invention in which the light delivery path and light collection path both pass through the medium of the front GRIN lens (are not physically segregated by a barrier therein), a front GRIN lens having a length less than 0.25 may be used to virtually eliminate such interference. Even though the front GRIN lens length used is shorter than the optimal length for measurements that occur at the surface of the GRIN lens, the light bends sufficiently before the shortened interface that the light is still focused to a point at least substantially the same size as if the lens is full length, 0.25 pitch. In embodiments in which no hole is drilled in the front common GRIN lens, i.e, there is no physical barrier between the light delivery and light collection paths within the front GRIN lens, the front GRIN lens may be less than 0.25 pitch and a silica, saphire or other low interference material may be used as a distal window to allow the focal point to be chosen at a depth from the distal end of the window. Usually the window is chosen so the probe can touch the material of interest and the optical sampling occurs just beyond of the window. In embodiments in which a hole is drilled in the front common GRIN lens and physical barrier is provided between the light delivery and light collection paths within the front GRIN lens, the front GRIN lens length used may for example be 0.25 pitch but is preferably less than 0.25 pitch, such as 5% shortened in length from 0.25 pitch to avoid interaction between the collection light path and the barrier.

The probe designs of the invention also allow for the use of multiple spectroscopic techniques and/or the introduction of other optical elements. Examples of other techniques that can be combined include florescence, Raman, OCT and reflectance spectroscopies. These measurements may occur from the same or approximately the same sample location. Other optical elements that may be utilized include polarization filters. For example, in the revolver-configured embodiments described herein, the collection channels may be configured to make different spectroscopic measurements.

The invention is further described with respect to the accompanying figures as follows.

Description of Embodiment Shown in FIGS. 1A-E

Since Raman spectroscopy probes are typically the most complex fiber optic probes to manufacture, an embodiment of a Raman probe to be operated at 785 nm laser is provided to illustrate the various features and advantages of the invention including the ease by which the various components can be properly aligned.

FIG. 1A shows a Raman spectroscopy probe embodiment of the invention including a front GRIN lens subassembly 100 including a common front GRIN lens and other components in a tube, a revolver-like subassembly 110 with a central longitudinal hole (shaft) there-through and four radially peripheral larger diameter holes there-through (the holes opening at the proximal and distal ends of revolver 110). The central hole in revolver 110 is sized to accept and house a light delivery subassembly 130 and each of the larger peripheral holes is sized to accept and house a light collection subassembly 120 (only one shown). The distal ends of the components are shown on the left and the proximal ends on the right in FIG. 1A. The outer diameter of the probe assembly shown as constructed is 3.4 mm. The major subassemblies are shown in an exploded view. In the assembled state front GRIN lens subassembly 100 and revolver 110 are butted up to each other, light delivery subassembly 130 is inserted into the central hole of the revolver and extend partially into the proximal end of front GRIN lens subassembly 100, and light collection subassembly 120 is inserted into a peripheral hole of revolver 110 so that its distal face is flush with the distal face of revolver 110. Each of the subassemblies is described in more detail below.

Figure 1B:
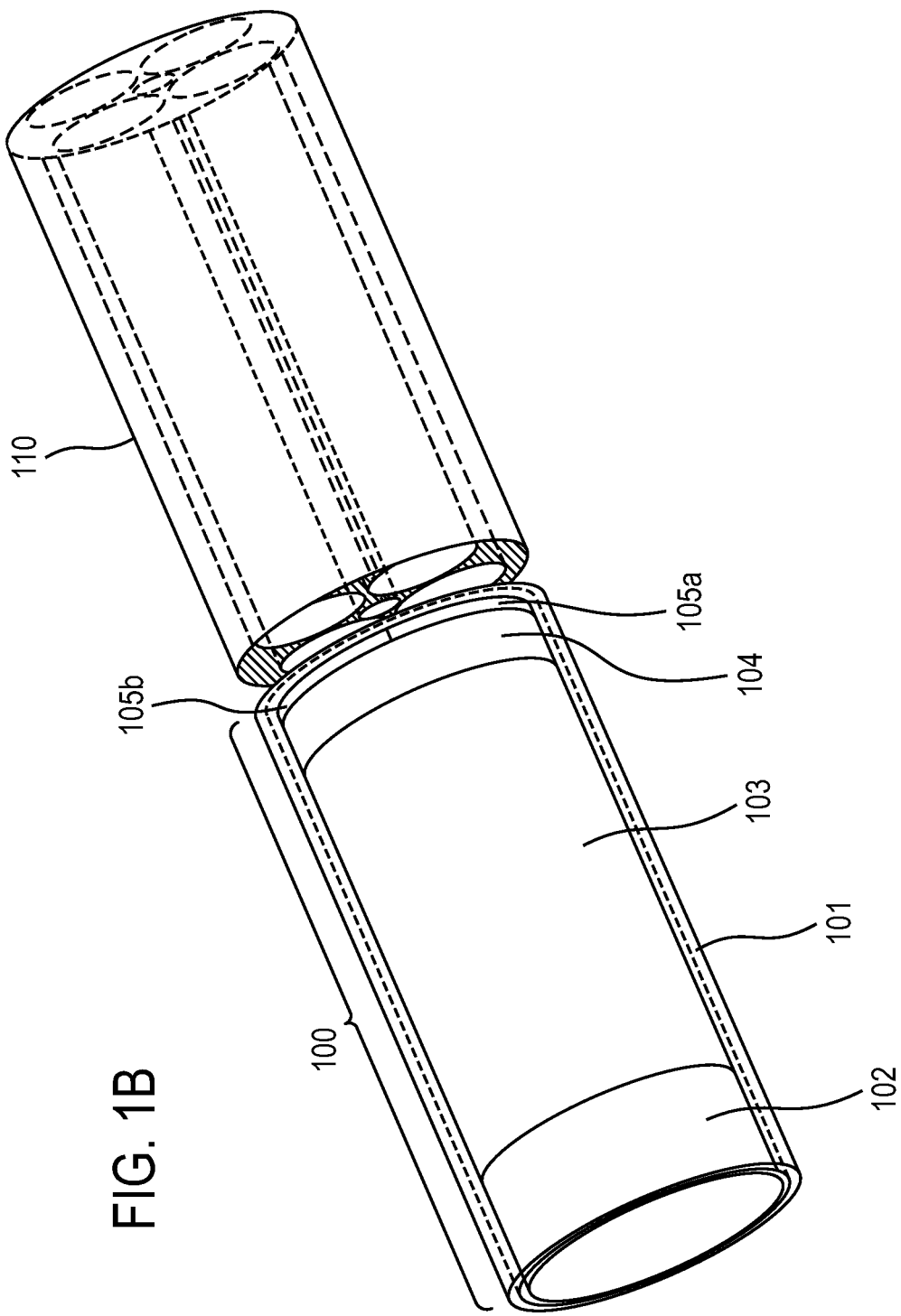
FIG. 1B: Revolver/common lens sub-assembly of embodiment shown in FIG. 1A.

FIG. 1B shows the front GRIN lens subassembly 100 and revolver 110 in more detail. The front GRIN lens 103 and optical window 102 are disposed within a tube 101. Proximal to the proximal end of front GRIN lens 103 is a donut-shaped long-pass filter 104 that optically communicates with the four peripheral shafts of the revolver member but not the central light delivery shaft thereof. Immediately proximal donut-shaped long-pass filter 104 are two half-donut polarization filters, 105a and 105b, each disposed over two of the peripheral shafts of revolver member 110. FIG. 1C shows a partially exploded view of FIG. 1B, each of the components being similarly numbered.

FIG. 1D shows light collection GRIN lens subassembly 120 in more detail. Outermost tube 121 surrounds and aligns the various components including, a collection GRIN lens 122 at the distal end. Tube 121 extends further proximally past the proximal end of collection GRIN lens 112 to receive the distal end of light collection optical fiber 124 which is surrounded by light collection optical fiber tube 123 which is sized to snuggly fit into tube 121. The collection optical fiber or optical fiber bundle/ferrule of the assembly is abutted to the proximal end of the collection GRIN lens. Tube 121 and light collection optical fiber tube 123 may each extend further proximally than shown to at or near the proximal end of optical fiber 124 (or corresponding optical fiber bundle if present).

Figure 1E:
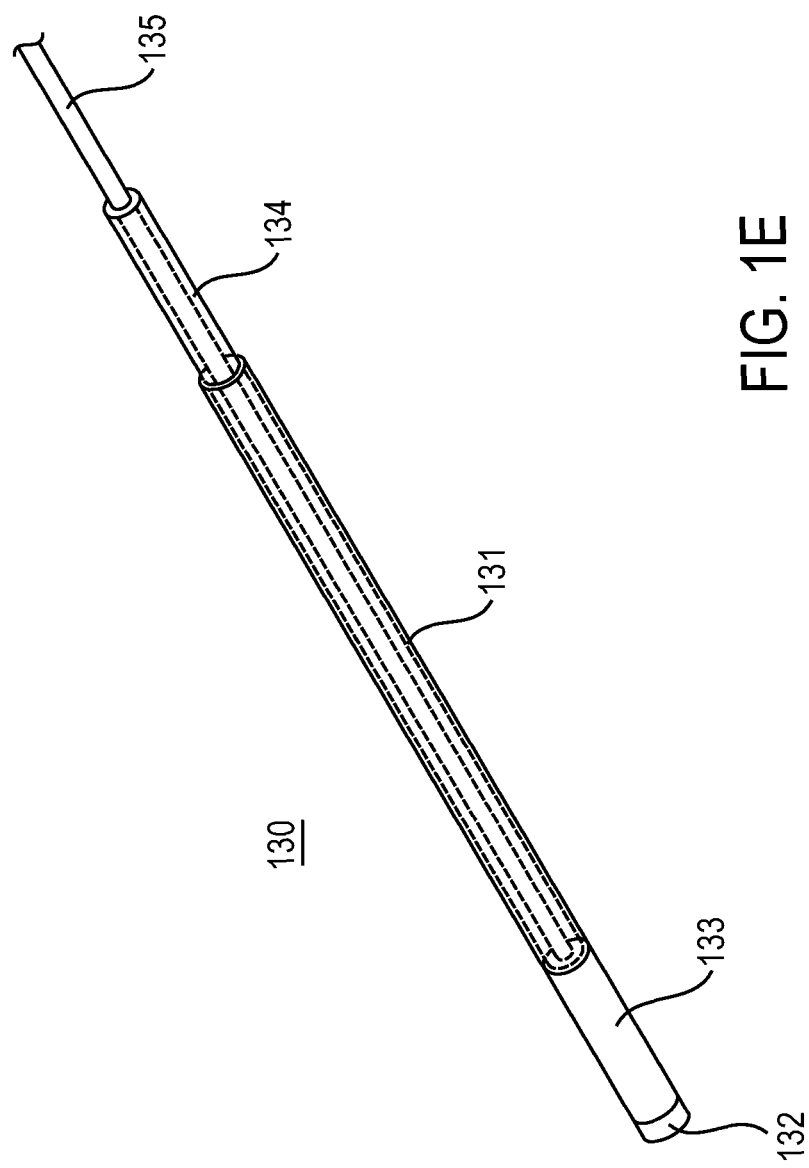
FIG. 1C: Exploded view of revolver/common lens sub-assembly of embodiment shown in FIG. 1A FIG. 1D: Collection sub-assembly of embodiment shown in FIG. 1A FIG. 1E: Laser lens delivery sub-assembly of embodiment shown in FIG. 1A FIG. 1F: Schematic diagram showing the position of components of the embodiment of FIG. 1A in the probe's assembled state.

FIG. 1E shows light delivery GRIN lens subassembly 130 in more detail. Outermost tube 131 surrounds, band-pass filter 132 at the distal end of the sub-assembly, and, proximal thereto, light delivery GRIN lens 133 and extends further proximally and receives light delivery optical fiber 135 surrounded by light delivery optical fiber tube 134 which is sized to snuggly fit within tube 131. Thus, the proximal end of bandpass filter 132 is in optical communication with the distal end of the light delivery GRIN lens and the proximal end of light delivery GRIN lens 133 is in optical communication with the distal end of light delivery optical fiber 135, the components being butted up to each other as shown. The use of nesting tubes facilitates the alignment and positioning of components in the light collection and light delivery subassemblies but is not required according to the invention.

Figure 1F:
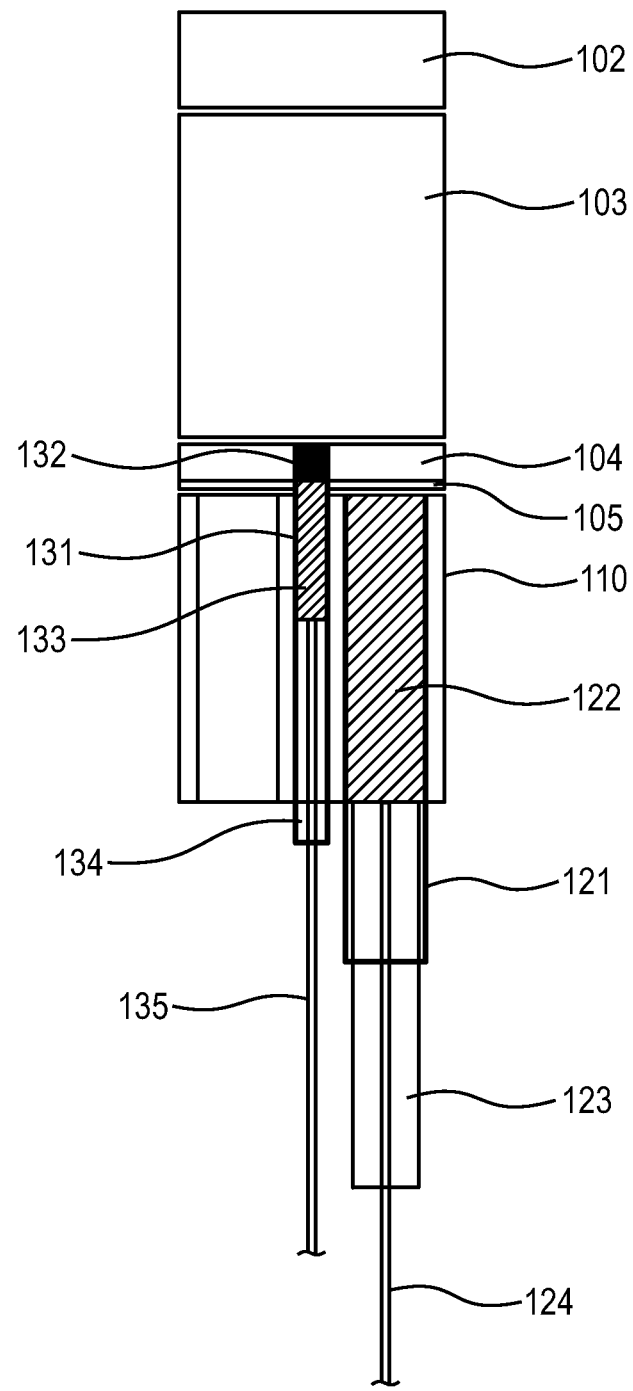

FIG. 1F is a schematic diagram showing the positions of the various aforementioned components of the probe assembly of the embodiment of FIG. 1A in its assembled state. The distal end of light delivery subassembly 130 extends beyond the distal end of revolver 110 and is disposed in channel formed by the central holes through the side-by-side half-donut polarization filters 105 and donut-shaped long pass filter 104. Some space is shown for the sake of clarity between window 102 and front GRIN lens 103, between front GRIN lens 103 and donut filter 104, and between half donut polarization filters 105 and revolver 110, but the aforementioned components may be flush against one another in the assembled probe. Outer front GRIN lens subassembly tube 101 is not shown but may be present. A separate outer tube be disposed over tube 101 and extend proximally to at least the proximal end of revolver 101.

Example of Manufacture and Assembly of an Embodiment of FIG. 1

To construct the laser lens delivery subassembly 130 shown in FIG. 1E, a single mode silica fiber 135 (Newport corporation) 5.4 micron mode field diameter/125 micron clad/245 micron acrylate buffer approximately two meters long is placed inside a stainless steel 26 ga regular wall tube 134 (0.010" (0.254 mm) ID, 0.018" (0.457 mm) OD) approximately 0.5" (12.7 mm) long with an optical epoxy, and heat cured according to the epoxy directions. The distal end of this fiber/tube assembly (135/134) is polished to a good quality optical finish, e.g., using approximately a 1 micron polish film or finer for the final polish. This polished fiber/tube (135/134) assembly is then placed inside a cleaned 0.0185" (0.470 mm) ID, 0.020" (0.508 mm) OD nitinol tube 131 (Memry Corp., Bethel, Conn., USA; OD obtained by centerless grinding of commercially available tube) approximately 0.5 (12.7 mm)" long with optical epoxy placed on the outside of the 0.018 (0.457 mm)" OD tube 134. Then a 0.25 pitch at 780 nm (approximately 2.7 mm long), 0.018" (0.457 mm) OD GRIN lens 133 (centerlessly ground down from a 1 mm OD GRIN lens, GoFoton, Japan; SELFOC micro lens), is placed inside nitinol tube 131 so that its proximal end abut the distal end of polished fiber/tube 135/134. A drop of optical epoxy is placed on the end of light delivery GRIN lens 133 and then a 785 nm bandpass filter 132 (Semrock Inc., Lake Forrest, Ill., USA) that has been core drilled to 0.018 (0.457 mm)" diameter and thinned to approximately 250 microns is abutted to the distal end of GRIN lens 133 (filter side down toward the lens). All the components are pushed together flush with distal end of filter 132 flush with the distal end of nitinol tube 131. Optical epoxy is used to secure all the components in place and is cured. If the end of band pass filter 132 is not flush with the distal end nitinol tube 131, the distal end of 132 can be polished to make sure all it is flush the distal end of tube 131.

The collection GRIN lens subassembly 120 shown in FIG. 1D may be assembled similarly to the light lens delivery subassembly 130. Seven 100 micron core/110 clad/125 buffer, low OH fibers (Polymicro Technologies, Phoenix, Ariz., USA) 124, approximately two meters long, are be placed inside a stainless steel tube 123 (0.015" (0.381 mm) ID, 0.047" (1.194 mm) OD) approximately 0.5" (12.7 mm) long with an optical epoxy and heat cured according to the epoxy directions. The distal end of fiber/tube 124/123 assembly is polished to a good quality optical finish, e.g., using approximately a 1-micron polish film or finer for the final polish. This polished fiber/tube 124/123 is then placed inside a cleaned 0.048" (1.219 mm) ID, 0.051" (1.295 mm) OD 17 ga thin wall hypodermic tube 121 that has been centerlessly ground, approximately 0.5" (12.7 mm) long with optical epoxy placed on the outside of the 0.047" (1.194 mm) OD polished tube 123 with fibers 124. Then a 0.25 pitch at 780 nm (at approximately 7.7 mm long), 0.047" (1.194 mm) OD GRIN lens 122 (centerlessly ground down from a 3 mm GoFoton SELFOC micro lens) is placed into the distal end of tube 121 to abut with the distal end polished fiber/tube 124/123. A drop of optical epoxy is placed on the end of GRIN lens 122. All these components are pushed together flush to the distal end of tube 121. Optical epoxy is used to secure all the components in place and is cured. If the distal end of GRIN lens 122 is not flush with distal end of tube, the distal end of GRIN lens 122 may be polished to make it flush therewith.

Revolver 110 may, for example, be machined from a brass cylinder, a different metal or alloy or any suitable material. The individual light delivery and light collection subassemblies are then placed inside the shafts of revolver 110. The light delivery subassembly 130 is sized for insertion into the central hole 0.02" (0.508 mm) of revolver 110, and the one or more light collection GRIN lens subassemblies (FIG. 1D) are inserted into the peripheral holes (0.052" (1.321 mm)) of revolver 110. The light delivery GRIN lens subassembly 130 protrudes from the distal end of revolver 110 the same distance as the thickness of long pass donut filter 104 plus any optical elements utilized like polarization filter 105a and 105b. Long pass donut filter 104 is positioned around the protruding distal end of light delivery subassembly 130 and in contact with the revolver 110 or other optical elements like polarization filter 105a and 105b. The distal end of the light collection GRIN lens subassembly 120 (FIG. 1D) is flush or approximately flush with the distal end of revolver 110.

In FIGS. 1B-C show the front GRIN lens subassembly 100 in more detail. Front GRIN lens 103 is a 3 mm diameter, 0.46 NA (GoFoton; SELFOC micro lens), shortened to, for example, 5 mm long. A fused silica window 102, 1.59 mm thick, 3 mm diameter is placed to the distal end of front common GRIN lens 103 using optical epoxy and cured. This GRIN lens (103) window (102) assembly is placed inside stainless steel tube 101 (0.119" (3.023 mm) ID, 0.134" (3.404 mm) OD) with optical epoxy and cured. The donut-shaped long pass filter 104 is placed on the proximal end of front GRIN lens 103 and affixed using optical epoxy and cured. Optical epoxy is placed at the ends (interfaces) of the inserted light collection GRIN lens subassemblies 130, distal end of revolver 110, long pass filter 104, and any other optical elements like polarization filter 105a and 105b, the window-lens-tube assembly, and cured.

The assembled probe end of the embodiment may, for example, then be placed inside a 4" long 9 ga extra thin wall needle tube 0.135" (3.429 mm) ID, 0.148" (3.759 mm) OD using optical epoxy filled with carbon black. After curing, the epoxy and tube are polished on the distal end to expose the silica window and yield a smooth flat distal end of the probe. Protective polymer tubes may be placed over the fibers, and connectors attached with epoxy, cured, and polished, as well known in the art. The other probe embodiments described herein may be similarly manufactured and assembled.

Further Discussion of Front, Common GRIN Lens Embodiments

For embodiments in which the illumination light and collection light are passed through a common front GRIN lens, this same lens focuses the delivered illumination light and collimates the collected light from the sample. If a probe is constructed using 1:1 imaging for the collection light, then the lens pair would use 1.8 mm diameter, 0.25 pitch, 0.46 NA GRIN lens for both lenses. However, using these collection and laser GRIN lenses would not allow for both light delivery and collection GRIN lenses to collectively physically fit behind (within the footprint of) the common front GRIN lens. Favorably, according to the invention, GRIN lenses can be altered to reduce their NA, by reducing their outer diameter, but still accept at least the majority to all or nearly all of the light a 0.22 NA fiber can accept. Additionally, this size reduction of the collection GRIN lens(es) allows for multiple collection lenses to be used thereby increasing the light gathering ability of the probe. The invention provides embodiments in which there is only one collection GRIN lens as well as embodiments in which there is more than one collection GRIN lens. For embodiments utilizing 1:1 imaging, the ability to have multiple collection GRIN lenses allows for significantly more light to be gathered compared to a probe with only one collection lens of the same dimensions coupled to 0.22 NA fiber(s). Where commercially available GRIN lens are of an outer diameter larger than that specified for a probe design according to the invention, the outer diameter can be reduced to specification, for example, by a preferred method of centerless grinding, or by longitudinally splitting the lens. These reductions in outer diameter, and thus NA, permit sufficient room to accommodate multiple collection GRIN lenses and a light/laser delivery GRIN lens behind the common front GRIN lens. Of course, GRIN lenses having particular NA values, such as 0.22 NA GRIN lenses (or any other NA desired) can also be custom manufactured. However, ground down GRIN lenses are still preferred (but not required) as non-ground-down manufactured GRIN lenses may have suboptimal performance at the outer edges leading to distortion.

These ground-down GRIN lenses may be placed in a tube, such as but not limited to a nitinol tube, which has the proper inner diameter (ID) to hold the lens, a very thin wall is preferable to keep the assembly small. Tube wall thicknesses may be reduced to desired values by centerless grinding if so desired or required for a particular application. An optical fiber or bunch of optical fibers can be placed in a tube/ferrule that has the same OD as the ground lens, polished to an optical finish, and placed in the nitinol tube to abut the lens. A brass or stainless steel rod may be machined to accept these lens tubes. This machined rod now resembles a revolver, i.e, a cylinder with one or more holes, e.g., cylindrical holes, passing from one end-face to the other, such as a central hole surrounded by a number of radially peripheral holes. In one variation, a narrow diameter cylindrical hole is formed in center of the revolver body to accommodate a laser delivery fiber assembly and a number of, such as four, larger diameter cylindrical holes surround the central hole to accommodate collection fiber assemblies. Thus, in this embodiment, the laser delivery lens tube would typically be placed in the smaller central hole, and the collection lens tubes would be placed in the larger outer holes which surround the central hole. Many other configurations within the scope of the invention are also possible as described herein and as may be apparent to those skilled in the art. The sizes of the outer peripheral holes are chosen to allow the collection GRIN lens to provide approximately 0.22 NA light to the 0.22 NA collection fiber(s), or similarly chosen to provide an at least substantially matching NA of light to whatever size collection optical fibers may be used. The size of the central hole is chosen to match the size of the light delivery lens tube which is chosen to be smaller than that of the collection lenses so that the maximum amount of light is collected while staying within the footprint of the common front lens. Where the light source is a laser, the best way to minimize the laser delivery tube/lens size is to use a single mode laser (Innovative Photonic Solutions, Monmouth Junction, N.J., USA) which has an output of approximately 0.11 NA. This allows the laser delivery GRIN lens to be ground down to a size smaller than 0.22 NA. Also, since the single mode laser can efficiently couple to a single mode fiber, such as that available from Newport Corporation, Irvine, Calif., USA (design wavelength 780 nm, mode field diameter of approximately 5.4 microns, and NA of 0.10 to 0.14) a light delivery GRIN lens with a 1 mm diameter start size may be chosen to be ground down allowing a very small diameter lens tube to be used The combination of a 1.8 mm front GRIN and a 1 mm laser GRIN will result in the image size of the laser delivery fiber to be increased. It is also possible to use one of the larger diameter outer lenses as a laser delivery channel with a 0.22 NA fiber (typically 100 micron core), wherein one or more of the other outer channels of the revolver are used for collection.

Each collection GRIN lens gathers light from an outer portion of the front common GRIN lens and therefore allows the collection of a large portion of the 0.46 NA, yet the light is converted to 0.22 NA which is fiber coupled. Therefore when using the same initial diameter front and collection GRIN lenses, higher NA light is able to be coupled into 0.22 NA fiber without an increase in the resulting image size. This allows the probe to collect significantly more light than any probe known which does not use multiple collection lenses. Advantageously, the described probe design acts as an NA converter while keeping the image size the same, unlike many other NA converters which have an image size change that reduces the performance of a spectrometer (resolution/light loss). The NA change occurs at the tip of the probe in a small form factor.

Embodiments having multiple collection GRIN lenses also allow for additional features not possible with a single lens probe such as the ability to selectively collect light from different angles from a target, utilizing multiple spectroscopies and collecting different polarization states.

Effect of Length of Front, Common GRIN Lens on Probe Performance

Figure 2A:
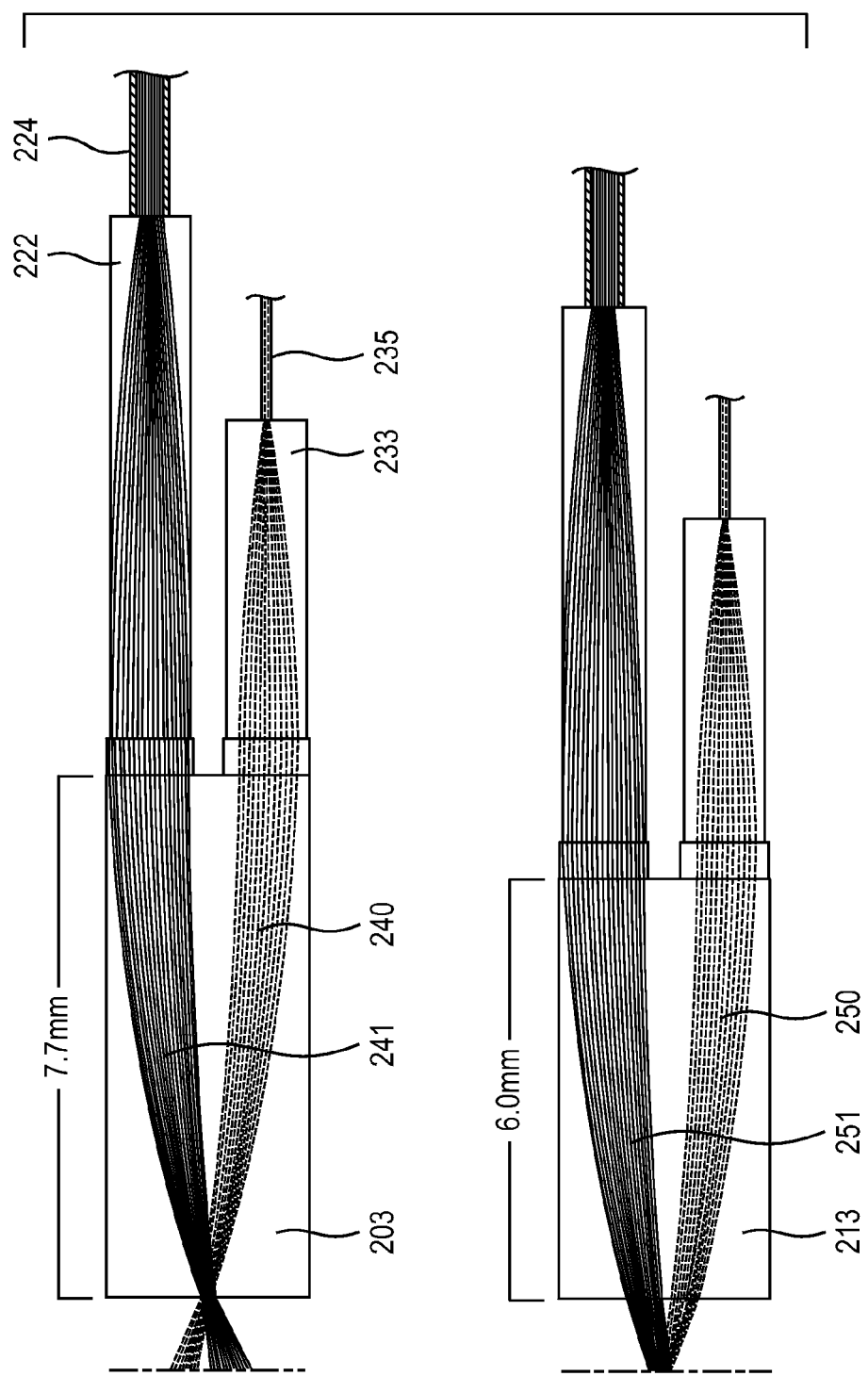
FIG. 2A: shows the effect of the length of the front GRIN lens of probe embodiments of the invention on the intersection of illumination and collection light paths in the front GRIN lens.
Figure 2B:
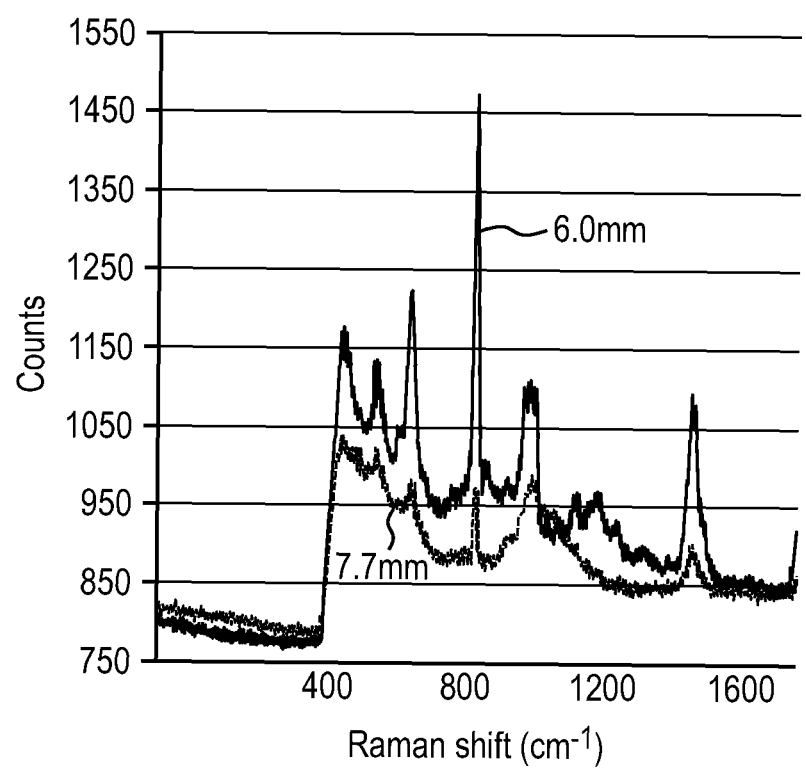
FIG. 2B: shows comparative spectra of a probe embodiment in which a GRIN lens is not sufficiently shortened vs. that for an embodiment in which the GRIN lens is sufficiently shortened, to prevent overlap of illumination and collection beams within the front GRIN lens.

FIGS. 2A and 2B illustrate the importance of selecting the proper length of front, common GRIN lens for various embodiments of the invention in which the illumination light and collection light both pass through a common front lens. The top panel of FIG. 2A shows a ray-trace diagram produced using Zemax software (Radiant ZEMAX LLC, Bellevue, Wash., USA, ZEMAX-EE) of an embodiment in which the front GRIN lens has a 0.25 pitch at 780 nm (illumination wavelength), corresponding to a length of approximately 7.7 mm. The embodiment shown is similar to that of FIG. 1, but in which both the light collection subassembly (light collection GRIN lens 222 and light collection fiber bundle 224) and light/laser delivery subassembly are disposed in outer, peripheral chambers of the revolver structure. As shown, in the embodiment of the top panel of FIG. 2A (7.7 mm front common GRIN lens length, 780 nm), the collection light path 241 and illumination light path 240 overlap within the common front GRIN lens 203, which unfavorably causes Raman spectra from the front GRIN lens itself to be included in and interfere with the collected sample signal.

The bottom panel of FIG. 2A shows a corresponding ray-trace diagram for a modified embodiment where the length of the front common GRIN lens is shortened to 6 mm. Advantageously, at this length, under the same test conditions (same sample, same illumination wavelength) there is no overlap of the illumination light path 250 and collection light path 251 within front GRIN lens 213 itself. FIG. 2B compares spectra obtained from an acrylic block sample at 19 mw power using the embodiments of FIG. 2A. As shown, a significantly stronger spectra was obtained from the sample using the 6 mm front GRIN lens embodiment than using the 7.7 mm (0.25 pitch) front GRIN lens the embodiment.

Comparative Performance of a Contact Probe According to the Invention Versus State of the Art Contact Probes All probes tested were designed as direct contact probes and operated at 785 nm laser wavelength. All the probes were tested with 19 mw of power delivered to the sample.

The test sample was designed to mimic tissue and test the depth specificity of the GRIN probe of the invention versus other probe designs. In medical applications gathering data from the first 200 micron can be very important. The probe may also be of a small diameter to allow for endoscopic and catheter-based applications. The sample was made using frosted, translucent polyethylene terephthalate (PET) to simulate scattering which would occur in biological tissue. More specifically, the test sample was a 170 micron thick frosted (translucent) PET polymer sheet adhered to a 3 mm thick clear acrylic block. The adhesive used to adhere the two materials was an acrylic based UV curable adhesive (Loctite 3106).

Figure 3A:
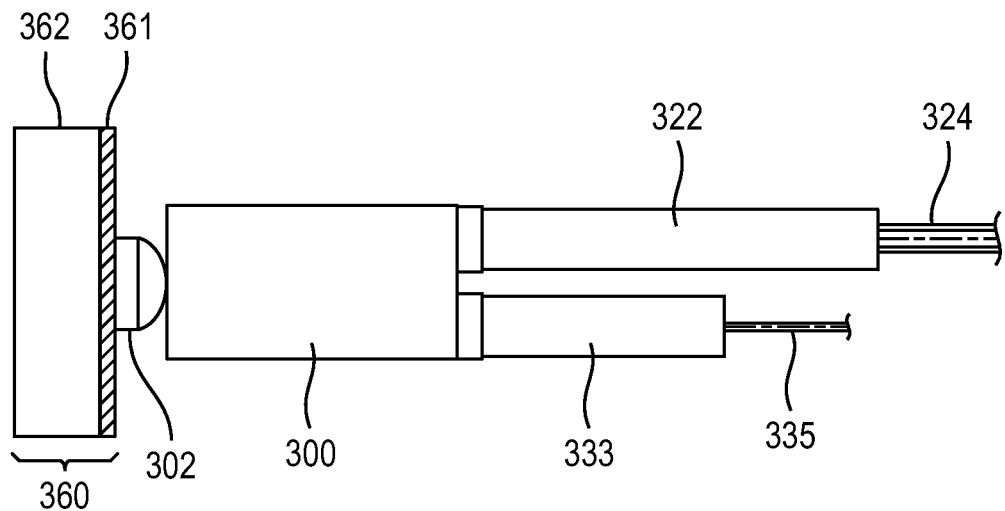
FIG. 3A shows the experimental set-up of a probe embodiment like that shown in FIG. 1A, in which only one of four collection channels was employed and the target sample used in the experiments.

A GRIN lens contact probe embodiment was configured for the comparative testing similar to the embodiment of FIG. 1, but including a front half-ball polishing lens distal to the front common GRIN lens to bring the focal volume within 200 microns of the distal end of the polishing lens, employing only one light collection subassembly, and using a peripheral hole of the revolver for the light delivery subassembly rather than the central hole of the revolver. A schematic diagram of the GRIN lens contact probe is shown in FIG. 3A. The rigid dimensions of the probe were 4.2 mm diameter and 10 cm-long, 8 gauge needle tube (this needle tube can be smaller diameter or length as needed). The laser delivery path uses 0.047" (1.194 mm) OD GRIN lens 333 (ground down from a 1.8 mm OD GRIN lens) and a 105-micron core, 0.22 NA laser fiber as the light delivery optical fiber 335. The light/laser delivery subassembly is placed in an outside channel of the revolver, causing the laser and collection beams to impinge at a greater angle than if the light/laser delivery subassembly was in the center channel of the revolver. This geometry samples a thinner volume which provides better depth resolution for this test. The collection GRIN lens 322 was 0.047" (1.194 mm) OD ground down from a 3 mm OD GRIN lens. A 6-around-1 bundle 324 of 100 micron core, 0.22 NA fibers (7 total fibers) were used as the collection fibers. A 3 mm OD 5.65 mm long common front GRIN lens 300 was used. A 2 mm diameter sapphire half ball/drum lens 302 was used to optimize collection in the first 200 microns of the sample (Zemax software was used to optimize the design prior to construction). For this test, only one collection GRIN lens was used out of the three possible for this configuration (since one peripheral channel of the revolver is occupied by the light/laser delivery subassembly). The sample 360 included a 170 micron layer of PET 361 adhered using an acrylic adhesive to an acrylic block backing 362.

A probe constructed according to U.S. Publication No. 2011/0135244 (non-lensed fiber probe) was the second probe tested (Emvision, Loxahatchee, Fla., USA; 24-around-1 Filtered Needle Probe, "the '244 Pub. probe"). This probe represents a previous state-of-the-art small diameter probe. This '244 Pub. probe can have a total of 24 (100 micron collection fibers), but to keep the light collection capability equivalent to that of the GRIN probe embodiment tested, only one third of the '244 probe collection fibers, i.e., 8 of the 24 collection fibers, were used.

An RPB Laboratory Probe (Inphotonics, Norwood, Mass., USA), which is a commercially available probe believed to be based on U.S. Pat. No. 5,112,127 was the third probe tested (the "Inphotonics probe"). This probe is quite large—indeed, all known confocal probes are large in comparison to the instant GRIN lens probe designs—but is used to illustrate the GRIN probe performance compared to other direct contact probe designs. The dimensions of the Inphotonics probe are: 4.2" (106.68 mm)L×1.5" (38.1 mm)W×0.5" (12.7 mm)T main probe body, with 1.5" (38.1 mm) long 0.375" (9.525 mm) diameter lens tube extending from the main body. A ball lens tube designed for contact with the sample was used. The Inphotonics probe utilizes a 90 micron excitation fiber and one 200 micron collection fiber. The full collection capabilities of this probe were tested.

Results of Comparative Testing:

Table 1 compares the results from each probe. For the calculations in Table 1, the largest peak height of the PET signal (at approximately 1600 wave numbers) was used. It was attempted to get the PET signal height equal for each probe by adjusting their acquisition times, but a 100-fold increase in the acquisition time for the '244 Pub. probe was deemed sufficiently long. The GRIN probe is superior in collecting the desired PET spectra compared to the two other probes tested. Notably, the GRIN probe spectra were obtained using only a one-second acquisition time, and the probe could collect even more light if one or more of the remaining available peripheral channels of the revolver were also provided with a light collection subassembly instead of the single light collection subassembly used in the experiment. The signal to noise ratio for the GRIN probe is superior to the other probes tested.

TABLE 1

| Probe | Acquisition time | PET signal height | Noise | Signal to noise ratio |
|---|---|---|---|---|
| GRIN probe | 1 second | 2911 | 26 | 112 |
| '244 Pub. | 100 seconds | 714 | 73 | 10 |
| Inphotonics | 8 seconds | 2922 | 56 | 52 |

Figure 3B:
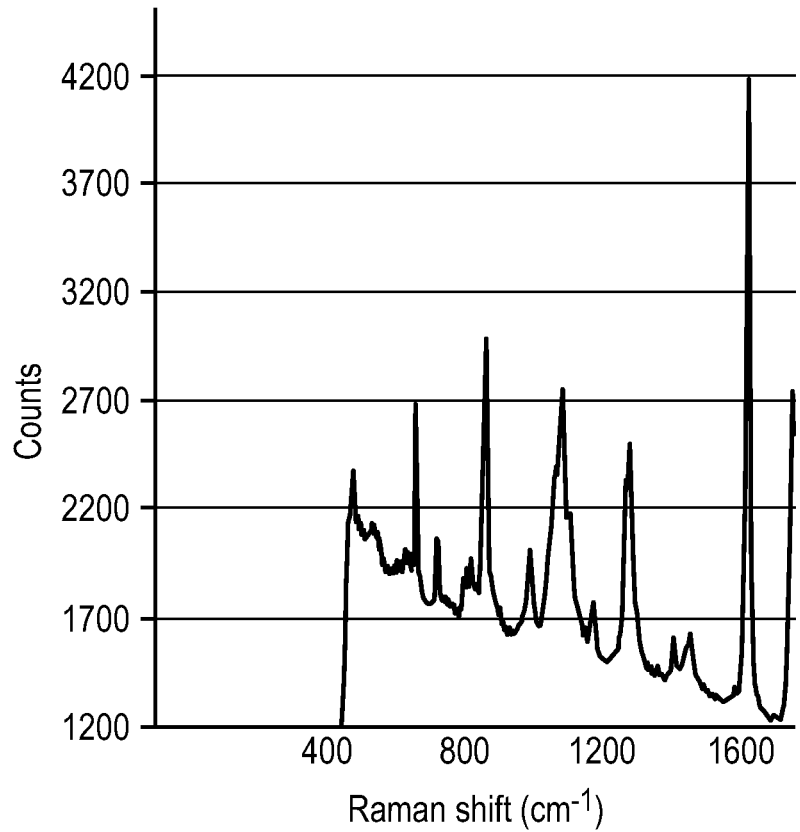
FIGS. 3B-3D show spectra obtained from the target sample using the probe of the embodiment shown in FIG. 3A as described and using other probe designs known in the art.
Figure 3C:
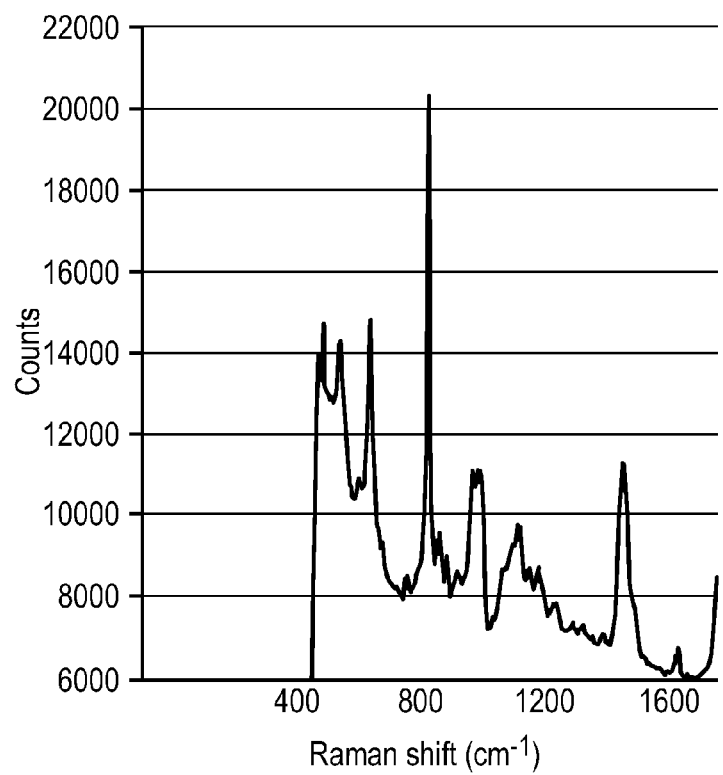
Figure 3D:
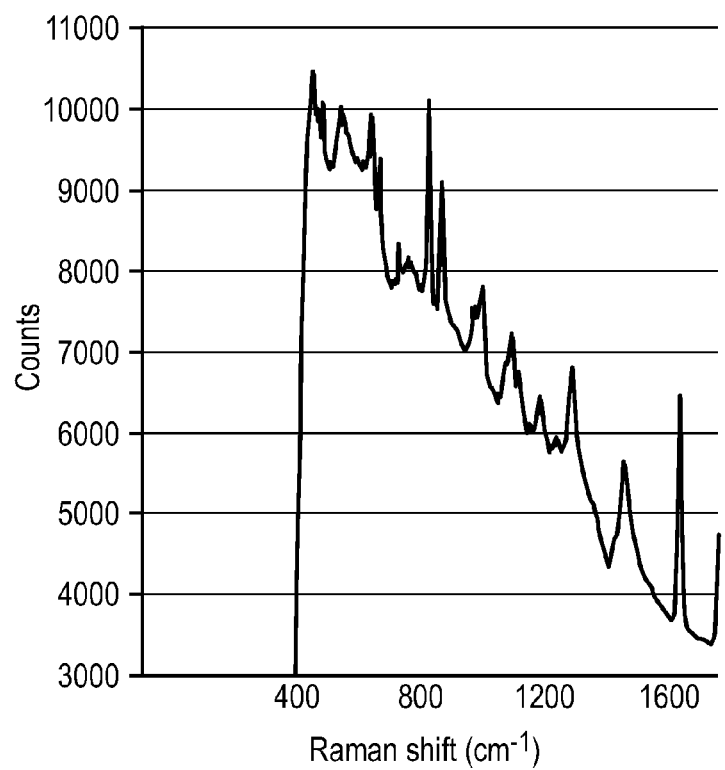
Figure 3E:
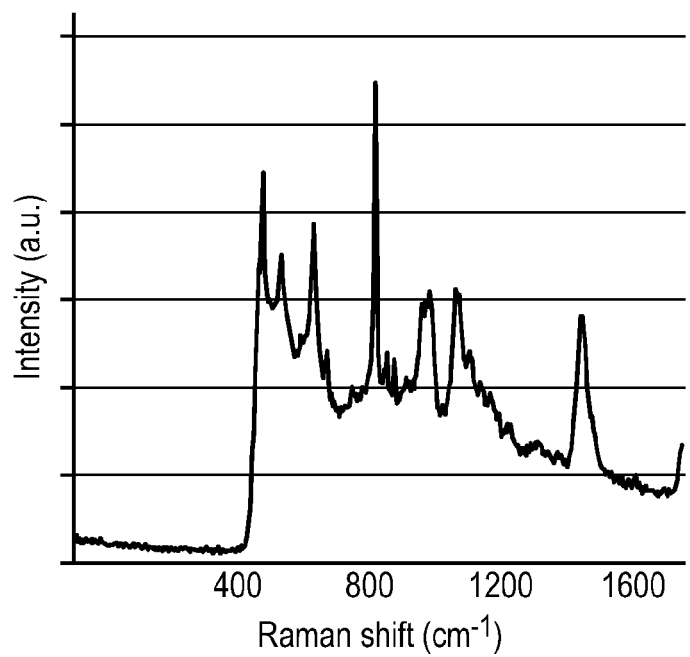
FIGS. 3E and 3F show reference spectra for the individual PET and acrylic components of the test sample.
Figure 3F:
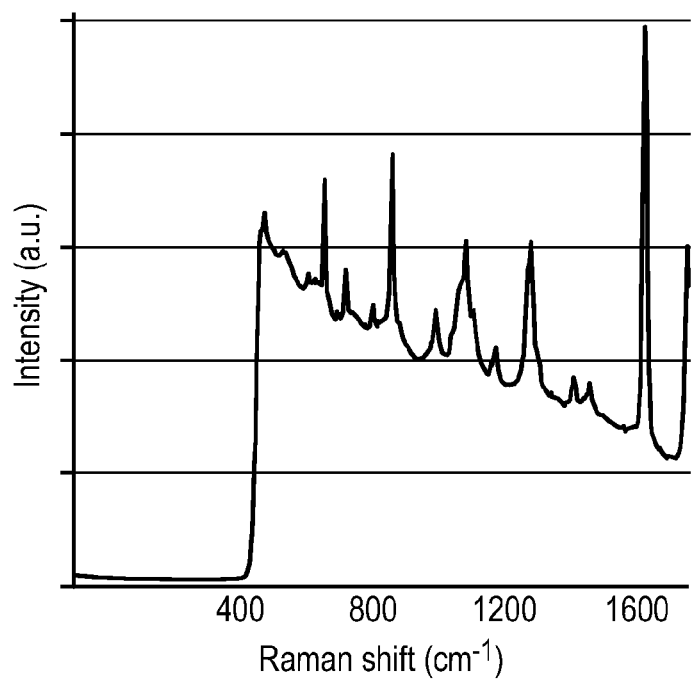

FIG. 3B shows the performance of the GRIN lens contact probe embodiment (of FIG. 3A) tested; it collected virtually all of the PET signal and very little acrylic signal. FIG. 3C shows the performance of the '244 Pub probe; this probe collected very little PET spectra, and mainly collected the acrylic spectra. FIG. 3D shows the performance of the Inphotonics probe; this probe collected a combination of PET spectra and the acrylic spectra. FIG. 3E shows a reference spectrum for the acrylic block backing only. FIG. 3F shows a reference spectrum for the PET test material only.

Embodiments with Physically Isolated Light Delivery Path

Figure 4A:
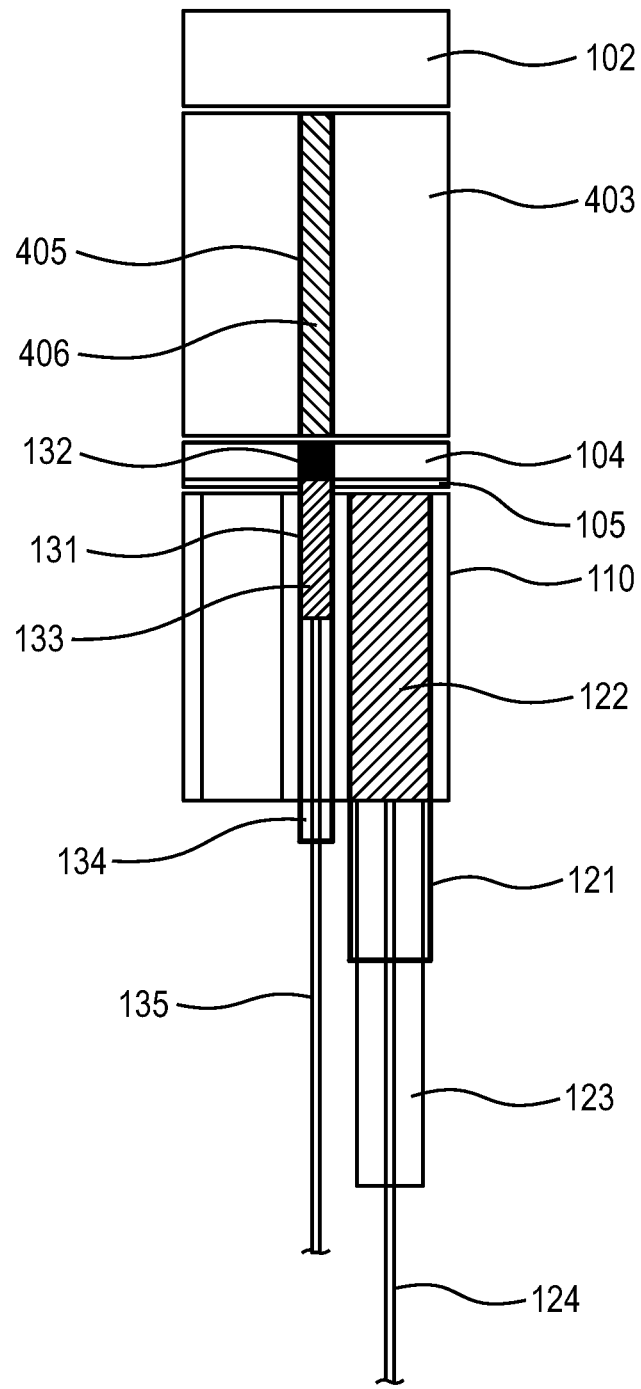
FIGS. 4A and 4B illustrate a probe embodiment of the invention in which a hole is drilled through the front GRIN lens and the light delivery subassembly is inserted in the hole

The invention also provides embodiments in which the light deliverypathway is confined in a separate tube, e.g., a metallic tube, which is inserted into a hole drilled in the front GRIN lens. In this manner, the delivery and collection light paths can be completely segregated with respect to all of the GRIN lenses and optical fibers. One such embodiment, configured for Raman spectroscopy, is schematically illustrated in FIG. 4A. The components of the embodiment shown are the same as those of the embodiment of FIG. 1F (and are numbered the same) except for the front GRIN lens 403 which has a central longitduinal hole drilled there-through (opening at each of the proximal and distal ends). Inserted into this hole is a tube 405 which is at least opaque to a preselected waveleight of light. The tube may, for example, be a metal tube that is generally opaque. Inserted within the tube is a front laser delivery GRIN lens. This is the same type of GRIN lens as front GRIN lens 403 having the same or approxomately the same refractive index gradient profile as the portion of the front GRIN lens 403 which was drilled out to form the hole. For example, the same precursor lens model used to make the front GRIN lens 403 or that which is selected to be front GRIN lens 403 can be machined to reduce its outer diameter down to that fitting snuggly within the inner diameter of the front laser delivery GRIN lens tube 405. In this type of embodiment, GRIN lens 133 which abuts the distal end of light delivery optical fiber 135 is referred to as the back light delivery GRIN lens. In a variation a single tube may be used in place of tube 131 and tube 405.

Figure 4B:
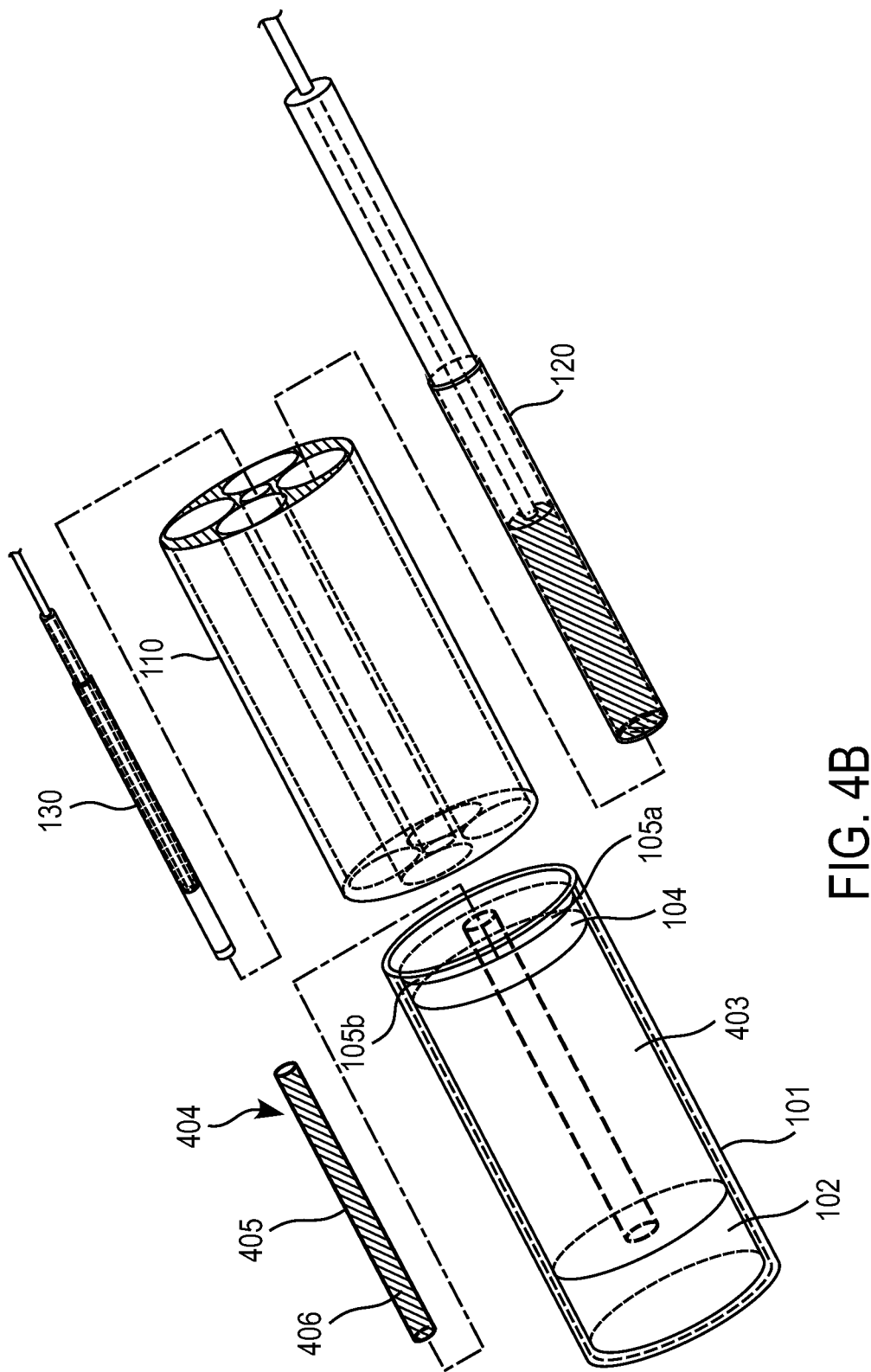

FIG. 4B shows a partially exploded view of the embodiment of FIG. 4B. The light deliveryGRIN lens tube 405 holds a front light delivery GRIN lens 406 which is the same type of lens but smaller diameter, i.e., has at least substantially the same refractive index gradient profile as the part of the front GRIN lens 403 that previously occupied the hole therein and length as the front GRIN lens. Tube 405 and front light delivery GRIN lens 406 inserted therein form a component 404 that is inserted into the central longitudinal hole formed in front GRIN lens 403. Where the front light delivery GRIN lens is to be placed in a hole through the center of the front GRIN lens, it can be manufactured, for example, by centerlessly grinding the same type of starting GRIN lens used to make the front GRIN lens, such as one with 3 mm original OD to a final 0.018" (0.457 mm) OD. A back light delivery GRIN lens 133 (proximal to the front light delivery GRIN lens) which is a 1 mm GRIN lens ground down to 0.018" (0.457 mm) OD is provided. A band-pass (BP) filter 132 is disposed between the front (406) and back (133) light delivery GRIN lenses in the light delivery pathway. This design completely isolates the light delivery path from the light collection path. The rest of the probe shown in FIG. 4B is the same as that of the probe embodiment shown in FIGS. 1A-F, with light delivery GRIN lens subassembly 130, one or more light collection GRIN lens subassemblies 120 and revolver 110. Various components within the front GRIN lens assembly may also be the same, for example, a long-pass (LP) donut filter 104 disposed between the front GRIN lens 403 and the collection GRIN lenses 122, and optional half-donut polarization filters 105a and 105b as well as outer tube 101

Embodiments with Drilled Collection GRIN Lens(es)

The invention also provides embodiments including a common, front GRIN lens as previously described and a collection GRIN lens behind (proximal to) the front GRIN lens, where the collection GRIN lens has a longitudinal hole provided therein, for example, by drilling, that is sized to accommodate and accommodates the light delivery fiber GRIN lens and optional distal component thereon such as band gap filter and whatever tube may surround them. The distal end of the light delivery optical fiber may also extend into the hole in the collection GRIN lens. In such embodiments as described, a separate revolver structure is not needed to align the light delivery and collection components. Instead, this function is performed by the collection GRIN lens itself. Typically, the distal end of the light delivery GRIN lens itself or any filter or component such as band pass filter disposed on the distal end of the light delivery GRIN lens will be longitudinally positioned within respect to the collection GRIN lens such that when the thickness of any optical components such as filters and polarizers are taken into account, the distal end of the light delivery GRIN lens or distal end of any component immediately adjoining it abuts the proximal end of the front GRIN lens. Further optionally, the light delivery fiber and its laser delivery GRIN lens and any distal components such as bandpass filter thereon may be encased in a tube, such as a metal tube, such that the entire encasement is disposed within the longitudinal hole in the collection GRIN lens—this provides a further material-based isolation of the light delivery and collection light paths within the collection GRIN lens.

Figure 5:
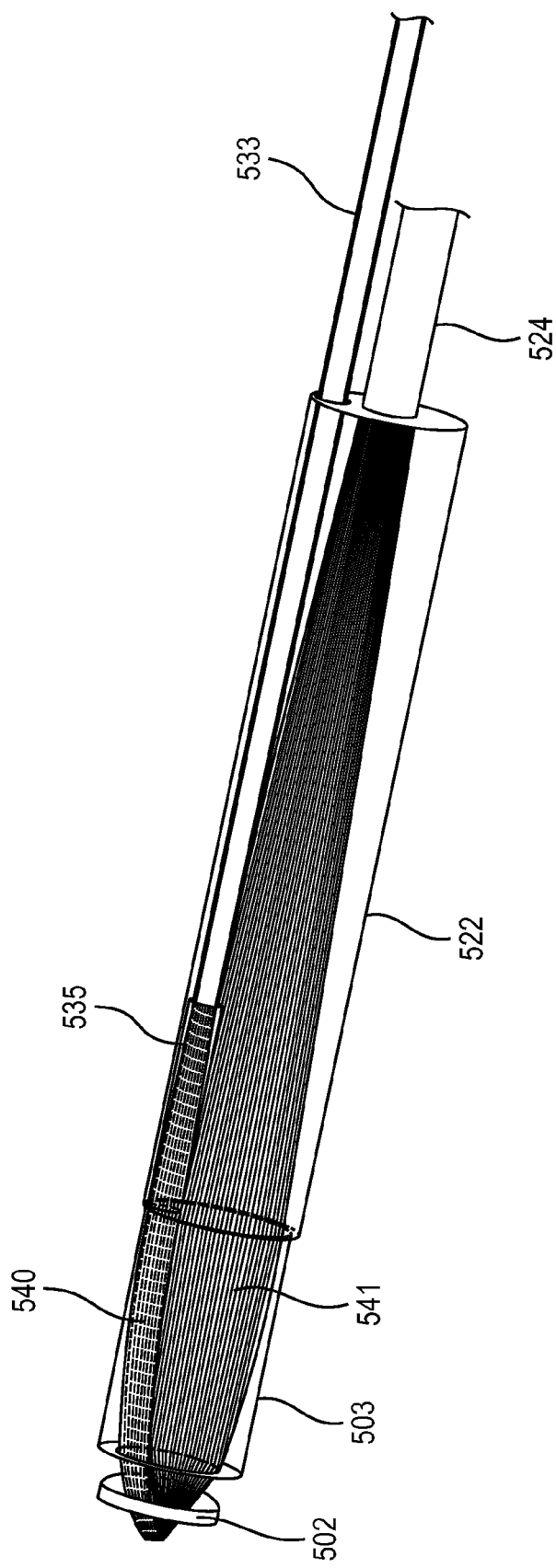
FIG. 5 illustrates a probe embodiment of the invention in which the light delivery components of the probe are inserted into a hole formed through the collection GRIN lens itself.

FIG. 5 illustrates one such embodiment. This embodiment has a front common 1.8 mm OD GRIN lens 503, a 0.022" (0.559 mm) OD light delivery GRIN lens 535 (ground down from a 1 mm OD GRIN lens) for the light delivery fiber 533, and a 1.8 mm OD GRIN collection GRIN lens 522 (ground down from a 4 mm OD GRIN lens). A longitudinal hole is drilled through the collection GRIN lens in which the light delivery subassembly passes and is disposed. An outer light delivery component tube, like 131 in FIG. 1E, may or may not be used. Depending on the diameter of light delivery optical fiber 533 with respect to the inner diameter of the hole, a light delivery fiber tube like 134 in FIG. 1E may desirable to align the fiber in the hole. As shown, the hole for the light delivery subassembly is disposed peripherally with respect to the center of the collection GRIN lens. The collection optical fiber(s) 524 is/are abutted to the proximal end of collection GRIN lens 522. This design increases the laser spot size and reduces the collection spot size. An optional half-ball optimizing lens 502 is provided distal to front common GRIN lens 503 to maximize illumination and light gathering from an area of interest, such but not limited to, within the first 200 microns beyond the optimizing lens. Lens 502 is a half-ball lens on to which an edge has been ground which allows it to be easily held by a tube (not shown). Those skilled in the art will understand that a variety of types of distal optimizing lenses and/or assemblies, such as side-viewing/illuminating assemblies can be employed for particular purposes and applications. Ray traces were produced using Zemax software for the illumination light path 540 and for the collection light path 541. There is virtually no_overlap between them within front common GRIN lens 503 with light delivery path 540 radially skirting light collection path 541.

Without limitation, the following embodiments and variations are provided by the invention.

One embodiment of the invention provides a fiber optic probe assembly having a distal sampling end and a proximal end, said probe including:

(a) a front (distal) GRIN lens having a distal end, a proximal end, a central (longitudinal) axis, a length and an outer diameter;

(b) at least one collection GRIN lens having a distal end, a proximal end, a central axis, a length and a outer diameter, the distal end of the at least one collection GRIN lens in optical communication with the proximal end of the front GRIN lens, (c) a collection optical fiber having a distal end, a proximal end and a central axis, the proximal end of at least one of the collection GRIN lenses being in optical communication with the collection optical fiber the central axis of the collection optical fiber at its distal end being parallel to the central axis of the front GRIN lens, and the transverse dimension (outer diameter) of the distal end of the collection optical fiber being within the footprint (outer diameter) of the front GRIN lens; and (d) a light delivery optical fiber having a distal end, a proximal end and a central axis, its central axis at its distal end being parallel to the central axis of the front GRIN lens and its transverse dimension (diameter) at its distal end being within the footprint (outer diameter) of the front GRIN lens.

By "footprint," what is meant herein is the meaning commonly understood in the art, i.e, the projection of the outer transverse dimension (that encompassed by a perimeter, such as the projection of an outer diameter) of a subject structure or face thereof, along its longitudinal axis in both directions such that something within the footprint could for example be falling within the footprint behind (proximal to) the proximal end/face of the structure or could be physically disposed within the actual outer transverse dimension of the structure, i.e., within the body of the structure. Various embodiments shown in the figures and described herein have been exemplified with optical components, such as the GRIN lenses, optical fibers and various tubes, having a circular transverse dimension (circular as to the perimeter of the cross-section). However, any of the various embodiments of the invention can be similarly implemented with components having different transverse dimension shapes, such as oval, polygonal, square, rectangular etc., alone or in combination with each other and/or circular cross-section components Thus, it should be understood that throughout this disclosure where "outer diameter" is referred to, "outer dimension" or "transverse dimension" for non-circular cross-section shaped components may be substituted and non-circular cross-section components may be used.

What is important for probes according to the invention is that the distal end of the one or more collection optical fibers (that optically communicate with the proximal end of the one or more collection GRIN lenses) and the distal end of the light delivery optical fiber or whatever component may be disposed distally thereon, such as a light delivery GRIN lens, are collectively within the footprint of the front GRIN lens. The collection GRIN lens(es) are at least partially within the footprint of the front GRIN lens so that collected light gathered by the front GRIN lens can be delivered into the collection GRIN lens. For example, the collection GRIN lens(es) may extend from within the footprint of the front GRIN lens to beyond it or may be completely within the footprint of the front GRIN lens. The light delivery GRIN lens, if present at the distal end of the light delivery optical fiber, is also at least partially within the footprint of the front GRIN lens.

Favorably, the outer dimensions of probes according to the invention may be very small, such as 4 mm OD or smaller. Thus, the invention provides miniature fiber optic probes that are well suited for endoscopic medical application among others.

In one variation, the distal end of the light delivery optical fiber is in optical communication with the proximal end of the front GRIN lens, one or more filters, lenses or polarizers optionally disposed provided there between. The length of the front GRIN lens may be selected to reduce or eliminate the overlap of light collection and light delivery pathways within the front GRIN lens for a preselected illumination wavelength of light. The front lens may be shortened to less than 0.25 pitch (from 0.25 pitch or greater than 0.25 pitch), based on the preselected illumination wavelength of light such as may be selected to perform a particular type of spectroscopy.

The embodiment may further include a light delivery GRIN lens having a distal end, a proximal end, a central axis, a length and an outer diameter, the proximal end of the light delivery GRIN lens in optical communication with the distal end of the light delivery optical fiber and the transverse dimension (outer diameter) of the light delivery GRIN lens being at least partially within the footprint (outer diameter) of the front GRIN lens.

The distal end of the light delivery GRIN lens may be in optical communication with the proximal end of the front GRIN lens, one or more filters optionally provided there between. As described before, the length of the front GRIN lens is selected to reduce or eliminate the overlap of light collection and light delivery pathways within the front GRIN lens for a preselected illumination wavelength of light. For example, the front GRIN lens maybe shortened to less than 0.25 pitch (from 0.25 pitch or greater than 0.25 pitch), based on the preselected illumination wavelength of light.

In another variation, at least one of the one or more collection GRIN lens and/or the light delivery optical fiber at its distal end is disposed radially off-axis with respect to the central longitudinal axis of the front GRIN lens. In a different variation, the distal end of the light delivery fiber is radially coaxial with respect to the central longitudinal axis of the front GRIN lens but the collection GRIN lens(es) is radially off-axis. In another variation, both the collection GRIN lens and the distal end of the light delivery optical fiber are radially coaxial with respect to the central longitudinal axis of the front GRIN In one version of the embodiment, a longitudinal hole is disposed in and passes through the center of the front GRIN lens, and the probe further includes:

a front laser delivery GRIN lens having a distal end and a proximal end surrounded by an optically opaque encasement inserted into said hole;

a back laser delivery GRIN lens having a distal end and a proximal end, the distal end thereof in optical communication with the proximal end of the front laser delivery GRIN lens and the proximal end thereof in optical communication with the distal end of the light delivery optical fiber; and optionally, one or more filters disposed between the front and back laser delivery GRIN lenses. The front laser delivery GRIN lens has at least substantially the same refractive index gradient profile as the portion of the front GRIN lens that existed in the space occupied by the hole before the hole was formed. The encasement may, for example, be a metal tube. The encasement may optionally extend further proximally to at least partially surround the back laser delivery GRIN lens, and optionally even further to surround at least part of the distal end of the light delivery optical fiber.

In a different version of the embodiment, a longitudinal hole is disposed in and passes through the front GRIN lens, for example, through the center, and the light delivery fiber is inserted into said hole such that the distal end of the light delivery fiber is disposed at or near the distal end of the front GRIN lens, the distal-proximal orientation of each of said components being codirectional. There may be no GRIN lens at all at the distal end of the light delivery fiber or at any point in the light delivery pathway. This version of the embodiment is particularly useful for fluorescence excitation and spectroscopy. In a variation, at least the part of the light delivery fiber inserted in the hold in the front GRIN lens is surrounded by an optically opaque tube, such as a metal tube. Optionally, the tube may extend further proximally.

In still another version of the embodiment, the probe further includes a light delivery GRIN lens having a distal end, a proximal end, a central axis, a length and an outer diameter, the proximal end of the light delivery GRIN lens in optical communication with the distal end of the light delivery optical fiber, wherein a longitudinal hole is disposed in and passes through a collection GRIN lens and the distal end of the laser delivery GRIN lens is inserted into said hole. In one variation of this version of the embodiment, there is a single collection GRIN lens selected to provide to the collection optical fiber/fiber bundle with which it optically communicates a collected light beam with a numerical aperture/diameter the same as or near the numerical aperture of said collection optical fiber.

For any of the probe assemblies, the numerical aperture of the front GRIN lens may be different than, such as greater than, the numerical aperture of at least one of the collection GRIN lenses. The numerical aperture of each of the collection GRIN lenses may, preferably, be at least substantially the same as the numerical aperture of the collection optical fiber/fiber bundle to which it is coupled. For any of the preceding probes, a collection GRIN lens may have a numerical aperture lower than that of the front GRIN lens with which it optically communicates and at least substantially the same numerical aperture as the collection optical fiber/fiber bundle with which it optically communicates.

In embodiments configured for Raman spectroscopy, a long-pass (LP) donut filter may be disposed around the laser lens tube prior to the window but after the front lens, and a band-pass (BP) filter disposed prior to the window but after the final laser lens. This configuration eliminates virtually any interference that may arise from a lens itself. Alternatively, for embodiments that uses a front common GRIN lens without a hole drilled through it, a donut-shaped LP filter may be disposed distal to this lens but proximal to a more distal window, and a BP filter for the light/laser delivery path disposed within the donut hole of the donut shaped LP filter. Thus, according to the invention, such as for Raman spectroscopy applications, the position of the various filters and other optical elements are not limited to being placed between the front GRIN lens and proximally disposed GRIN lens(es). Advantageously, the radial location of a collection subassembly with respect to the footprint of the front GRIN lens may be initially selected during design and/or selected/changed during operation to permit different angles of light to be collected as desired. For example, in embodiments having a revolver-structure hosting multiple light collection subassemblies in the channels of the revolver, collection of light from particular collection subassemblies represents light collected from different angles. This property also permits embodiments to be designed de novo wherein the various collection subassemblies provide particular predetermined angles of light collection.

A related embodiment provides a fiber optic probe assembly having a distal sampling end and a proximal end, that includes:

(a) a front GRIN lens (which is either the only one or a first one) having a distal end, a proximal end, a central longitudinal axis, a length and an transverse dimension;

(b) at least one light collection GRIN lens having a distal end, a proximal end, a central axis, a length and a transverse dimension, the distal end of the at least one collection GRIN lens in optical communication with the proximal end of the front GRIN lens; and (c) a light collection optical fiber having a distal end, a proximal end, a transverse dimension and a central axis, the proximal end of at least one of the collection GRIN lenses being in optical communication with the distal end of the collection optical fiber, the central longitudinal axis of the collection optical fiber at its distal end being parallel to the central axis of the front GRIN lens, and the transverse dimension of the collection optical fiber at its distal end being within the footprint of the front GRIN lens. The front GRIN lens may be shorter than 0.25 pitch for a preselected wavelength of light. The numerical aperture of the front GRIN lens may greater than the numerical aperture of the at least one collection GRIN lens.

The probe assembly of this embodiment may further include:

a second front GRIN lens having a distal end, a proximal end, a central longitudinal axis, a length and an transverse dimension, the central axes of the first and second front GRIN lens being parallel to each other; and a light delivery optical fiber having a distal end, a proximal end, a transverse dimension and a central longitudinal axis, the central longitudinal axis of the light delivery optical fiber at its distal end being parallel to the central longitudinal axis of the second front GRIN lens, the distal end of the light delivery optical fiber in optical communication with the proximal end of the second front GRIN lens, the transverse dimension of the light delivery optical fiber being within the footprint of the second front GRIN lens. This version of the embodiment not only encompasses the type of probe assembly shown in FIGS. 4A and 4B, but also includes probe assemblies where the separate front GRIN lenses are positioned side-by-side rather than one inserted into a hole in the other. The separate front GRIN lenses may, for example, be formed by longitudinally splitting a precursor GRIN lens, the two (or more) resulting sections being arranged in their original orientation with respect to each other. Alternatively, appropriate separate front GRIN lenses may be individually selected and/or machined for use in the same probe assembly. For example, two or more of the same model precursor GRIN lenses can be machined, such as by grinding and/or polishing to form separate GRIN lenses that represent longitudinal sections of the precursor GRIN lens. These separate lens sections, which are separate GRIN lenses, may be "reassembled" to form a partitioned front GRIN lens assembly. A physical partition such as a thin strip, such as a metal or polymer strip may, for example, be placed between the two (or more) front GRIN lenses to physically isolate them from each other in the probe assembly. The separate front GRIN lenses as described may have the same length.

In any of the probe assemblies, the longitudinal axes of the front GRIN lens(es), and the collection GRIN lens(es) may be parallel. Where there is more than one front GRIN lens, their longitudinal axes may be parallel. Where there is more than one collection GRIN lens, their longitudinal axes may be parallel. All of the longitudinal axes of the front GRIN lens (es), the collection GRIN lens(es), the distal ends of the light collection optical fiber(s), the distal ends of any light delivery optical fibers, and any light delivery GRIN lens(es) may be parallel. A light collection GRIN lens may be at least partially within the footprint of a front GRIN lens with which it optically communicates, such as partially within or fully within the footprint of the front GRIN lens.

The invention also provides catheters such as intravascular catheters that include any of the fiber optic probe assemblies described herein such as at or near the distal insertion end of the catheter. Such catheter-based embodiment may be configured for side-viewing and/or side-illumination, for example, using a mirror or prism as known in the art.

The invention further provides spectroscopy apparatuses that include: any of the probe embodiments, versions and variations thereof described herein; a light analyzer optically linked to the at least one collection optical fiber of the probe; and a light source optically linked to the at least one delivery optical fiber of the probe assembly. The light analyzer may, for example, be selected from the group consisting of a light detector, a spectrometer and an interferometer. The light source may, for example, be a laser or a non-coherent light source depending on the type(s) of spectroscopy which it is desired to practice. The apparatus may further include at least one computer including at least one computer processor and computer accessible memory comprising computer instructions for controlling the at least one light source and/or at least one light detector/analyzer and/or for recording and/or analyzing data from the at least one light analyzer, said computer being operably linked to the at least one light source and/or at least one light detector/analyzer, for example, as commonly known in the art. The computer may further include at least one user input device such as a keyboard and/or at least one user output device for example a display and/or a printer.

Apparatuses according to the invention may, for example, be configured to perform one or more of: Raman spectroscopy, such as finger print Raman spectroscopy and/or high-wavenumber Raman spectroscopy, diffuse reflectance spectroscopy, specular reflectance spectroscopy, fluorescence spectroscopy such as time-resolved fluorescence spectroscopy and UV fluorescence spectroscopy, infrared spectroscopy, laser-induced breakdown spectroscopy (LIBS) and optical coherence tomography (OCT).

Another embodiment of the invention provides a method for manufacturing a fiber optic probe assembly having a distal sampling end and a proximal end that includes the steps of:
providing a front GRIN lens having a distal end, a proximal end, a central axis, a length and an outer diameter (transverse dimension);
providing at least one collection GRIN lens having a distal end, a proximal end, a central axis, a length and an outer diameter (transverse dimension);
providing a light delivery optical fiber having a distal end, a proximal end and a central axis and an outer diameter (transverse dimension), wherein optionally a light delivery GRIN lens having a distal end, a proximal end, a central axis, a length and an outer diameter (transverse dimension) is provided and optically coupled to the distal end of the light delivery optical fiber;
providing a light collection optical fiber for each collection GRIN lens, said fiber having a distal end, a proximal end, a central axis and an outer diameter (transverse dimension);
optically coupling the distal end of each collection GRIN lens to the proximal end of the front GRIN lens; and
optically coupling the distal end of a light collection optical fiber to the proximal end of each collection GRIN lens,
wherein the outer diameters (transverse dimensions) of all the collection optical fibers and light delivery optical fibers at their distal ends collectively fit within (are disposed within) the footprint (outer diameter; transverse dimension) of the front GRIN lens.

The methods of the invention are not limited to any particular order of performance of the method steps and none should be inferred except those obviously logically necessitated, such as an article being first provided before it is later acted upon.

In one variation of the method, the step of providing the at least one collection GRIN lens further includes reducing the outer diameter (transverse dimension) of at least one precursor GRIN lens to a final outer diameter (transverse dimension), which may include or consist essentially of centerlessly grinding the precursor GRIN lens to reduce its outer diameter (transverse dimension).

In another variation of the method, the step of providing the front GRIN lens further includes reducing the outer diameter (transverse dimension) of at least one precursor GRIN lens to a final outer diameter (transverse dimension), which may include or consist essentially of centerlessly grinding the precursor GRIN lens to reduce its outer diameter (transverse dimension).

In a further variation, the step of providing the front GRIN lens further includes shortening a precursor GRIN lens from an initial length to the length of the front GRIN lens used in the assembly. This shortening may, for example, be from a length of or greater than 0.25 pitch to a length less than 0.25 pitch, such as but not limited to 5% less than 0.25 pitch, the pitch being determined with respect to a wavelength of light of interest, i.e., that which is desired to use with the probe for a particular application. The shortening of the precursor GRIN lens is readily accomplished by machining, such as grinding or polishing.

One version of the method embodiment further includes the steps of:
providing a light delivery GRIN lens having a distal end, a proximal end, an outer diameter and a length; and
optically coupling the proximal end of the light delivery GRIN lens to the distal end of the light delivery optical fiber. This version of the method may further include the step of optically coupling the distal end of the light delivery GRIN lens to the proximal end of the front GRIN lens. The step of optically coupling the distal end of the light delivery optical fiber to the proximal end of the front GRIN lens may further include: forming a longitudinal hole through a collection GRIN lens; and inserting the light delivery GRIN lens into said hole, such that the proximal-distal orientation of said components is codirectional and the distal end of the light delivery GRIN lens is disposed at or near the distal end of the collection GRIN lens. The method may further include the step of providing and optically coupling a filter such as a band-pass filter to the distal end of the light delivery optical fiber. In one variation of this version, there is only one collection GRIN lens. The step of providing the laser delivery GRIN lens or any optional distal filter components to be disposed thereon may further include the step of first providing a larger outer diameter precursor component and reducing its outer diameter to that used in the assembly as previously described. As previously described, the numerical aperture of each collection GRIN lens may be at least substantially the same as the light collection optical fiber/fiber bundle to which it is coupled.

A different version of the method embodiment further includes the steps of:

forming a longitudinal hole having an inner diameter and passing through the front GRIN lens, such as by drilling;

providing a front laser delivery GRIN lens having at least substantially the same refractive index profile as the portion of the front GRIN lens that previously occupied the hole in the front lens and at least substantially the same length as the front GRIN lens, and having a proximal and distal end and a outer diameter smaller than the inner diameter of the hole;

providing a back laser delivery GRIN lens having a distal end, a proximal end, an outer diameter and a length;

optically coupling the proximal end of the front laser delivery GRIN lens to the distal end of front laser delivery optical GRIN lens;

optically coupling the distal end of the back laser delivery GRIN lens to the proximal end of the front laser delivery GRIN lens;

optically coupling the proximal end of the back laser delivery GRIN lens to the distal end of the light delivery optical fiber;

inserting the front laser delivery GRIN lens in the hole formed in the front GRIN lens, such that the front laser delivery GRIN lens is surrounded therein by the tube; and optionally surrounding the front laser delivery GRIN lens in a tube that is optically opaque to a preselected wavelength of light, said tube optionally extending proximally to surround at least part of the back laser delivery GRIN and optionally extending further proximally to surround at least part of the laser delivery optical fiber. When the front laser delivery GRIN lens is surrounded by the tube, it may for example, be done prior to inserting the front laser delivery GRIN lens into the hole in the front GRIN lens.

It should be readily understood from the examples provided herein that the proximal-distal orientations of all the components are consistently codirectional in the various sub-assemblies, assemblies and finished probes and are never opposite each other. Thus, for this variation, while it is easier to insert the distal end of the front laser delivery fiber into the hole at the proximal end of the front GRIN lens and move it distally to its final position, it could nevertheless be similarly positioned by first passing the proximal end of the attached laser delivery optical fiber into the hole at the distal end of the front GRIN lens and moving is proximally until the front laser delivery GRIN lens and coupled components reach their final position.

The method may include further steps of preparing any of the various GRIN lenses as previously described. The step of surrounding the front laser delivery GRIN lens in the tube, may further include: providing a precursor tube having an inner diameter sized to accommodate the outer diameter of the front laser delivery GRIN lens and an initial outer diameter larger than the inner diameter of the longitudinal hole formed in the front GRIN lens; and reducing the outer diameter of the precursor tube to a final outer diameter sized for insertion into the longitudinal hole formed in the front GRIN lens. Reducing the outer diameter of the precursor tube may include or consist of centerlessly grinding it to reduce its outer diameter.

In a different version of the embodiment, the method includes the steps of: forming a longitudinal hole passing through front GRIN lens, for example, at the center thereof: and inserting the light delivery fiber into said hole such that the distal end of the light delivery fiber is disposed at or near the distal end of the front GRIN lens, the distal-proximal orientation of each of said components being codirectional. There may be no GRIN lens at all at the distal end of the light delivery fiber or at any point in the light delivery pathway. As previously described, probe assembly so-formed is particularly useful for fluorescence excitation and spectroscopy. In a variation, at least the part of the light delivery fiber inserted in the hole in the front GRIN lens is surrounded by an optically opaque tube, such as a metal tube. Optionally, the tube may extend further proximally. The light delivery optical fiber may, for example, be first inserted into the tube and then the tube-surrounded light delivery optical fiber can be inserted into the hole in the front GRIN lens.

A related embodiment of the invention provides a method for manufacturing a fiber optic probe assembly having a distal sampling end and a proximal end that includes the steps of:

providing a front GRIN lens having a distal end, a proximal end, a central axis, a length and an outer diameter (transverse dimension);

providing at least one collection GRIN lens having a distal end, a proximal end, a central axis, a length and an outer diameter (transverse dimension);

providing a light collection optical fiber for each collection GRIN lens, said fiber having a distal end, a proximal end, a central axis and an outer diameter (transverse dimension);

optically coupling the distal end of each collection GRIN lens to the proximal end of the front GRIN lens; and optically coupling the distal end of a light collection optical fiber to the proximal end of each collection GRIN lens, wherein the outer diameters (transverse dimensions) of all the collection optical fibers and light delivery optical fibers at their distal ends collectively fit within (are disposed within) the footprint (outer diameter; transverse dimension) of the front GRIN lens.

In one variation of this method embodiment, the step of providing the at least one collection GRIN lens further includes reducing the outer diameter of at least one precursor GRIN lens to a final outer diameter, which may include or consist essentially of centerlessly grinding the precursor GRIN lens to reduce its outer diameter.

In another variation of this method embodiment, the step of providing the front GRIN lens further includes reducing the outer diameter (transverse dimension) of at least one precursor GRIN lens to a final outer diameter (transverse dimension), which may include or consist essentially of centerlessly grinding the precursor GRIN lens to reduce its outer diameter (transverse dimension)

In a further variation of this method embodiment, the step of providing the front GRIN lens further includes shortening a precursor GRIN lens from an initial length to the length of the front GRIN lens used in the assembly. This shortening may, for example, be from a length of or greater than 0.25 pitch to a length less than 0.25 pitch, such as but not limited to 5% less than 0.25 pitch, the pitch being determined with respect to a wavelength of light of interest, i.e., that which is desired to use with the probe for a particular application.

Any of the optical surfaces of components of probe assemblies of the invention may also be coated with anti-reflective (AR) coatings, as desired.

Each of the patent applications, patents and other publications cited in this disclosure is incorporated by reference as if fully set forth herein. Various of the manufacturing and assembly techniques, such as those relating to alignment and filters, that may be employed for the present invention are discussed in detail in co-owned U.S. application Ser. No. 12/630,640 filed Dec. 3, 2009 for "Filtered Fiber Optic Probe" (U.S. Pub. No. 2011/0135244) which is incorporated by reference in its entirety herein.

Although the invention has been described in connection with specific preferred embodiments, it should be understood that the invention as claimed should not be unduly limited to such specific embodiments. Indeed, various modifications of the described modes for carrying out the invention which may be apparent to those skilled in the art upon reading this disclosure are intended to be within the scope of the following claims.

What is claimed is:

1. A fiber optic probe assembly having a distal sampling end and a proximal end, said probe comprising:
    (a) a front GRIN lens having a distal end, a proximal end, a central axis, a length and a transverse dimension;
    (b) at least one collection GRIN lens having a distal end, a proximal end, a central axis, a length and a transverse dimension, the distal end of the at least one collection GRIN lens in optical communication with the proximal end of the front GRIN lens,
    (c) a collection optical fiber having a distal end, a proximal end a central axis and a transverse dimension,
        the proximal end of at least one of the collection GRIN lenses being in optical communication with the collection optical fiber
        the central axis of the collection optical fiber at its distal end being parallel to the central axis of the front GRIN lens, and
        the transverse dimension of the collection optical fiber at its distal end being within the footprint of the front GRIN lens; and
    (d) a light delivery optical fiber having a distal end, a proximal end and a central axis, its central axis at its distal end being parallel to the central axis of the front GRIN lens and its transverse dimension at its distal end being within the footprint of the front GRIN lens.

2. The probe assembly of claim 1, wherein the distal end of the light delivery optical fiber is in optical communication with the proximal end of the front GRIN lens.

3. The probe assembly of claim 2, wherein the length of the front GRIN lens is selected to reduce or eliminate the overlap of light collection and light delivery pathways within the front GRIN lens for a preselected illumination wavelength of light.

4. The probe assembly of claim 3, wherein the front lens is shorter than 0.25 pitch, based on the preselected illumination wavelength of light.

5. The probe assembly of claim 1, further comprising a light delivery GRIN lens having a distal end, a proximal end, a central axis, a length and a transverse dimension, the proximal end of the light delivery GRIN lens in optical communication with the distal end of the light delivery optical fiber and the transverse dimension of the light delivery GRIN lens being at least partially within the footprint of the front GRIN lens.

6. The probe assembly of claim 5, wherein the distal end of the light delivery GRIN lens is in optical communication with the proximal end of the front GRIN lens.

7. The probe assembly of claim 6, wherein the length of the front GRIN lens is selected to reduce or eliminate the overlap of light collection and light delivery pathways within the front GRIN lens for a preselected illumination wavelength of light.

8. The probe assembly of claim 7, wherein the front GRIN lens is shorter than 0.25 pitch, based on the preselected illumination wavelength of light.

9. The probe assembly of claim 1, wherein at least one of (i) a collection GRIN lens and (ii) the light delivery fiber at its distal end is disposed radially off-axis with respect to the central longitudinal axis of the front GRIN lens.

10. The probe assembly of claim 5, wherein at least one of (i) a collection GRIN lens and (ii) the light delivery GRIN lens is disposed radially off-axis with respect to the central longitudinal axis of the front GRIN lens.

11. The probe assembly of claim 1, wherein a longitudinal hole is disposed in and passes through the center of the front GRIN lens, and further comprising:
    a front laser delivery GRIN lens having a distal end and a proximal end inserted into said hole, said front laser delivery GRIN lens optionally surrounded by a tube in said hole;
    a back laser delivery GRIN lens having a distal end and a proximal end, the distal end thereof in optical communication with the proximal end of the front laser delivery GRIN lens and the proximal end thereof in optical communication with the distal end of the light delivery optical fiber; and
    optionally, one or more filters provided between the front and back laser delivery GRIN lenses.

12. The probe assembly of claim 11, wherein the front laser delivery GRIN lens has at least substantially the same refractive index gradient profile as the portion of the front GRIN lens that existed in the space occupied by the hole before the hole was formed.

13. The probe assembly of claim 11, wherein the front laser delivery GRIN lens is surrounded by the tube and optionally the back laser delivery GRIN lens is at least partially surrounded by the tube.

14. The probe assembly of claim 5, wherein a longitudinal hole is disposed in and passes through a collection GRIN lens and the distal end of the laser delivery GRIN lens is inserted into said hole.

15. The probe assembly of claim 14, wherein there is a single collection GRIN lens selected to provide to the collection optical fiber with which it optically communicates collected light at the proximal end of the collection GRIN lens, the collected light having an outer diameter the same as or near the numerical aperture of the collection optical fiber.

16. The probe assembly of claim 1, wherein the numerical aperture of the front GRIN lens is not the same as the numerical aperture of at least one of the collection GRIN lenses.

17. The probe assembly of claim 5, wherein the numerical aperture of the front GRIN lens is not the same as the numerical aperture of at least one of the collection GRIN lenses and the laser delivery GRIN lens.

18. The probe assembly of claim 1, wherein the numerical aperture of each of the collection GRIN lenses is at least substantially the same as the numerical aperture of the collection optical fiber to which it is coupled.

19. The probe assembly of claim 5, wherein the numerical aperture of the laser delivery GRIN lens is at least substantially the same as the numerical aperture of the laser delivery optical fiber to which it is coupled.

20. The probe assembly of claim 1, wherein a collection GRIN lens has a numerical aperture lower than that of the front GRIN lens with which it optically communicates and has at least substantially the same numerical aperture as the collection optical fiber with which it optically communicates.

21. The probe assembly of claim 1, wherein
a longitudinal hole is disposed in and passes through the front GRIN lens,
the light delivery fiber is inserted into said hole such that the distal end of the light delivery fiber is disposed at or near the distal end of the front GRIN lens, the distal-proximal orientation of each of said components being codirectional, and
optionally at least the portion of the light delivery fiber inserted into the hole in the front GRIN lens is surrounded by a tube.

22. The probe assembly of claim 1, wherein the distal end of the light delivery fiber is not optically coupled to a GRIN lens.

23. A spectroscopy apparatus comprising:
a probe assembly according to claim 1;
a light analyzer optically linked to the at least one collection optical fiber of the probe assembly; and
a light source optically linked to the at least one delivery optical fiber of the probe assembly.

24. The apparatus of claim 23, wherein the light analyzer is selected from the group consisting of a light detector, a spectrometer and an interferometer.

25. The apparatus of claim 23, wherein the light source is a laser.

26. A fiber optic probe assembly having a distal sampling end and a proximal end, said probe comprising:
(a) a front GRIN lens having a distal end, a proximal end, a central longitudinal axis, a length and an transverse dimension;
(b) at least one collection GRIN lens having a distal end, a proximal end, a central axis, a length and a transverse dimension, the distal end of the at least one collection GRIN lens in optical communication with the proximal end of the front GRIN lens; and
(c) a collection optical fiber having a distal end, a proximal end, a transverse dimension and a central axis,
the proximal end of at least one of the collection GRIN lenses being in optical communication with the collection optical fiber,
the central longitudinal axis of the collection optical fiber at its distal end being parallel to the central axis of the front GRIN lens, and
the transverse dimension of the collection optical fiber at its distal end being within the footprint of the front GRIN lens.

27. The probe assembly of claim 26, wherein the front GRIN lens is shorter than 0.25 pitch for a preselected wavelength of light.

28. The probe assembly of claim 27, wherein the numerical aperture of the front GRIN lens is greater than the numerical aperture of the at least one collection GRIN lens.

29. The probe assembly of claim 26, wherein the numerical aperture of the front GRIN lens is greater than the numerical aperture of the at least one collection GRIN lens.

30. The probe assembly of claim 26, further comprising:
a second front GRIN lens having a distal end, a proximal end, a central longitudinal axis, a length and a transverse dimension, the central axes of the first and second front GRIN lens being parallel to each other and the first and second front GRIN lenses being positioned side-by-side; and
a light delivery optical fiber having a distal end, a proximal end, a transverse dimension and a central longitudinal axis,
the central longitudinal axis of the light delivery optical fiber at its distal end being parallel to the central longitudinal axis of the second front GRIN lens,
the distal end of the light delivery optical fiber in optical communication with the proximal end of the second front GRIN lens, and
the transverse dimension of the light delivery optical fiber being within the footprint of the second front GRIN lens.

* * * * *